United States Patent
Burdeniuc et al.

(10) Patent No.: US 11,208,519 B2
(45) Date of Patent: Dec. 28, 2021

(54) REACTIVE AMINE CATALYSTS FOR POLYURETHANE APPLICATIONS

(71) Applicant: Evonik Operations GmbH, Essen (DE)

(72) Inventors: Juan Jesus Burdeniuc, Colmar, PA (US); Torsten Panitzsch, Henstedt-Ulzburg (DE); Kai Xi, The Woodlands, TX (US); Renee Jo Keller, Orwigsburg, PA (US)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/160,225

(22) Filed: Oct. 15, 2018

(65) Prior Publication Data
US 2019/0048121 A1    Feb. 14, 2019

Related U.S. Application Data

(63) Continuation of application No. 15/170,142, filed on Jun. 1, 2016, now Pat. No. 10,100,141.

(60) Provisional application No. 62/169,046, filed on Jun. 1, 2015.

(51) Int. Cl.
| | | |
|---|---|---|
| C07C 273/18 | (2006.01) | |
| C08G 18/18 | (2006.01) | |
| C08G 18/32 | (2006.01) | |
| C08G 18/65 | (2006.01) | |
| C08G 18/76 | (2006.01) | |
| C08J 9/14 | (2006.01) | |

(52) U.S. Cl.
CPC .... *C08G 18/1825* (2013.01); *C07C 273/1809* (2013.01); *C08G 18/1841* (2013.01); *C08G 18/3203* (2013.01); *C08G 18/657* (2013.01); *C08G 18/7621* (2013.01); *C08J 9/142* (2013.01); *C08G 2110/0008* (2021.01); *C08G 2110/0083* (2021.01); *C08J 2205/06* (2013.01); *C08J 2375/04* (2013.01)

(58) Field of Classification Search
CPC ............... C08G 18/1825; C08G 18/18; C08G 18/1808; C08G 2101/0008; C08J 2205/06; C08J 2375/04
See application file for complete search history.

(56) References Cited

U.S. PATENT DOCUMENTS

| | | |
|---|---|---|
| 4,049,591 A | 9/1977 | McEntire et al. |
| 4,101,470 A | 7/1978 | McEntire |
| 5,859,079 A | 1/1999 | Mercando et al. |
| 6,232,356 B1 | 5/2001 | Mercando et al. |
| 6,596,663 B1 | 7/2003 | Tamano et al. |
| 6,858,654 B1 | 2/2005 | Wendel et al. |
| 8,367,870 B2 | 2/2013 | Burdeniuc et al. |
| 9,334,382 B2 | 5/2016 | Burdeniuc et al. |
| 2001/0044516 A1* | 11/2001 | Kaufhold ............ C08G 18/6674 528/65 |
| 2012/0178839 A1 | 7/2012 | Burdeniuc et al. |
| 2013/0065978 A1* | 3/2013 | Burdeniuc ............... C08K 5/31 521/117 |

FOREIGN PATENT DOCUMENTS

| | | |
|---|---|---|
| CN | 1201801 A | 12/1998 |
| EP | 1092737 A2 | 4/2001 |
| JP | S5350110 A | 5/1978 |
| JP | S644613 A | 1/1989 |
| JP | 2009108035 A | 5/2009 |
| WO | 2015095683 A1 | 6/2015 |

* cited by examiner

*Primary Examiner* — Melissa A Rioja
(74) *Attorney, Agent, or Firm* — Andrew H. Chung; Linda S. Li; Jason S. Ngui

(57) ABSTRACT

Tertiary amine catalysts having isocyanate reactive groups that are capable of forming thermally stable covalent bonds able to withstand temperatures up to 120° C. are disclosed. These catalyst can be used to produce polyurethane foam having the following desirable characteristics: a) very low chemical emissions over a wide range of environmental conditions and isocyanate indexes (e.g., indexes as low as 65 but higher than 60) while meeting all physical property requirements; b) sufficient hydrolytic stability to maintain the catalyst covalently bound to foam without leaching of tertiary amine catalyst when foam is exposed to water or aqueous solutions even at temperatures higher than ambient (temperature range 25° C. to 90° C.); and c) stable contact interface between the polyurethane polymer and other polymers (for example polycarbonate) with minimal migration of tertiary amine catalyst from polyurethane polymer to other polymers yielding no noticeable polymer deterioration at the point of contact even under conditions of heat and humidity.

10 Claims, 6 Drawing Sheets

Figure 1: Index 90 Foam Specimens in Contact with Polycarbonate
Dabco®33LV (Foam 5)
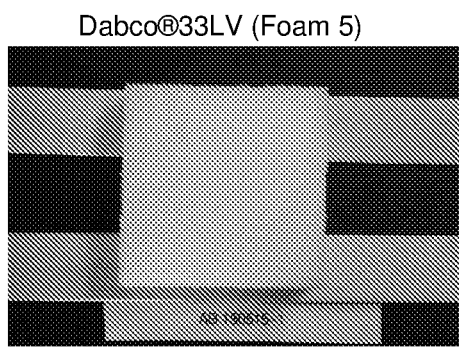
Dabco®1070 (Foam 6)
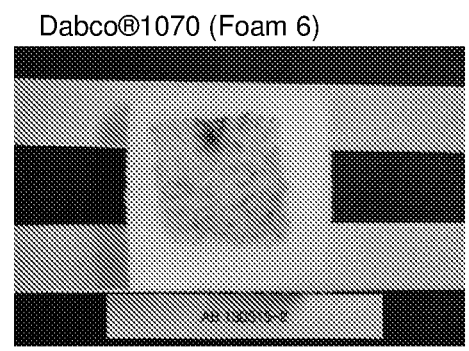
Amine-4 (Foam-8)
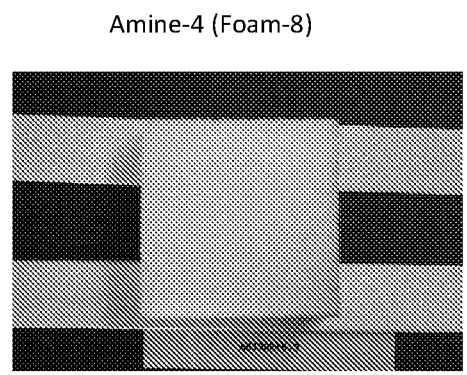
Amine-3 (Foam-7)
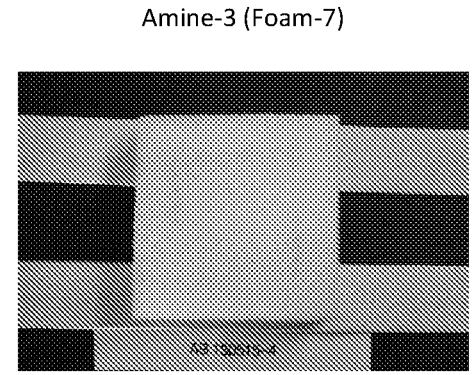

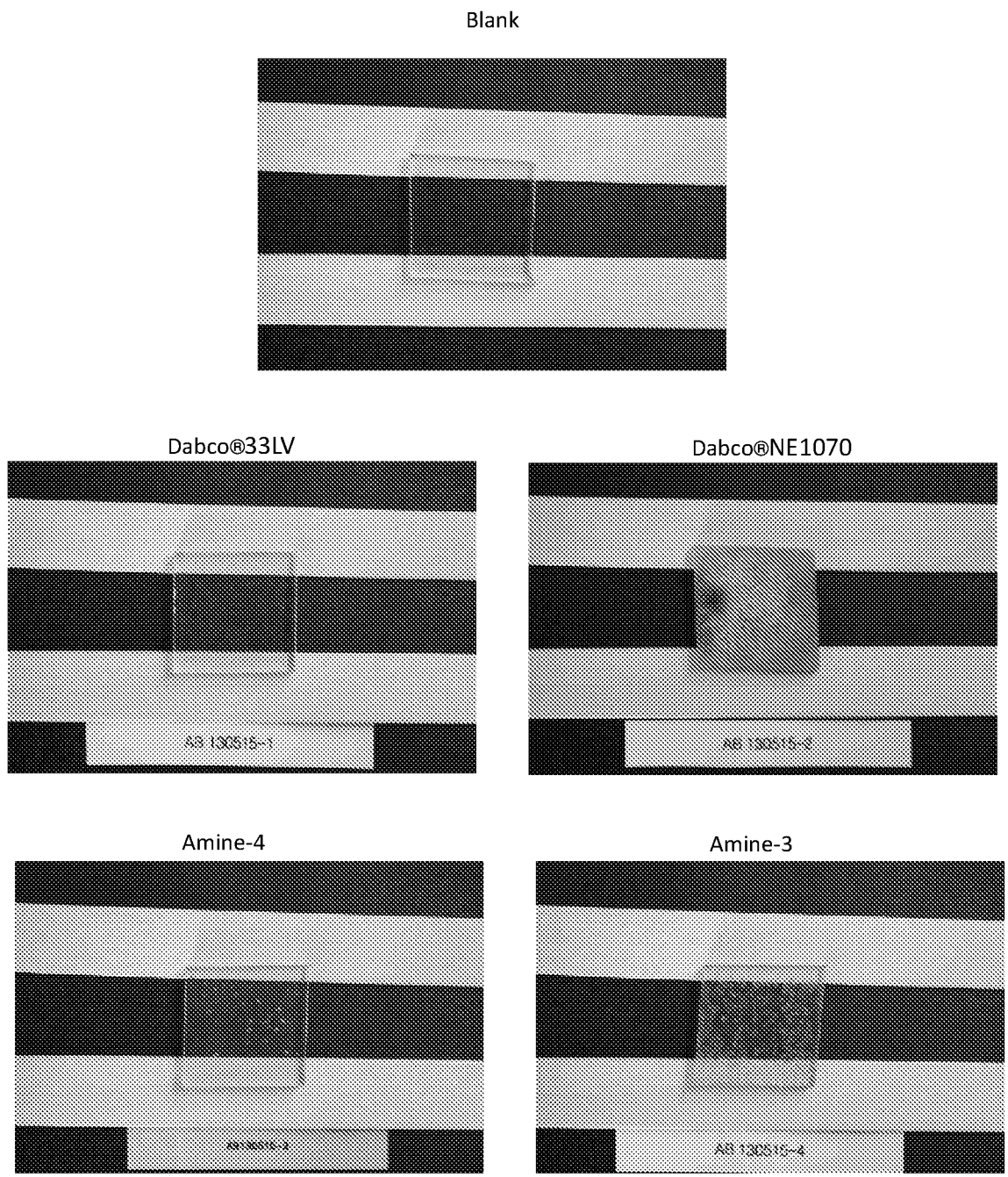
Figure 2: Index 90 Polycarbonate Specimens in Contact with Foam

Figure 3: Index 65 Foam Specimens in Contact with Polycarbonate
Dabco®33LV (Foam-1)
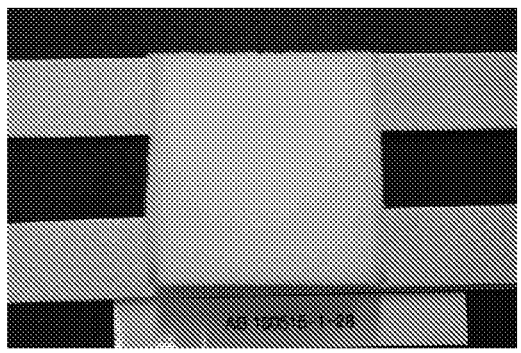
Dabco®NE1070 (Foam-2)
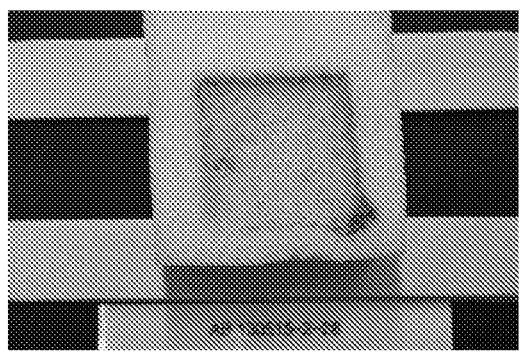
Amine-4 (Foam-4)
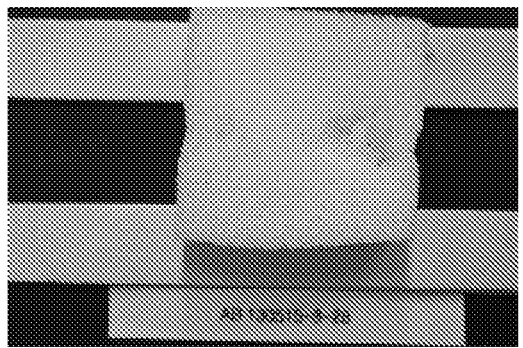
Amine-3 (Foam-3)
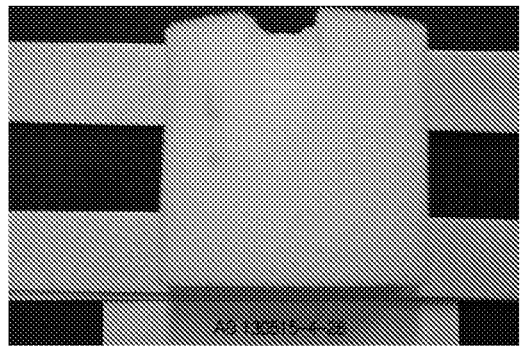

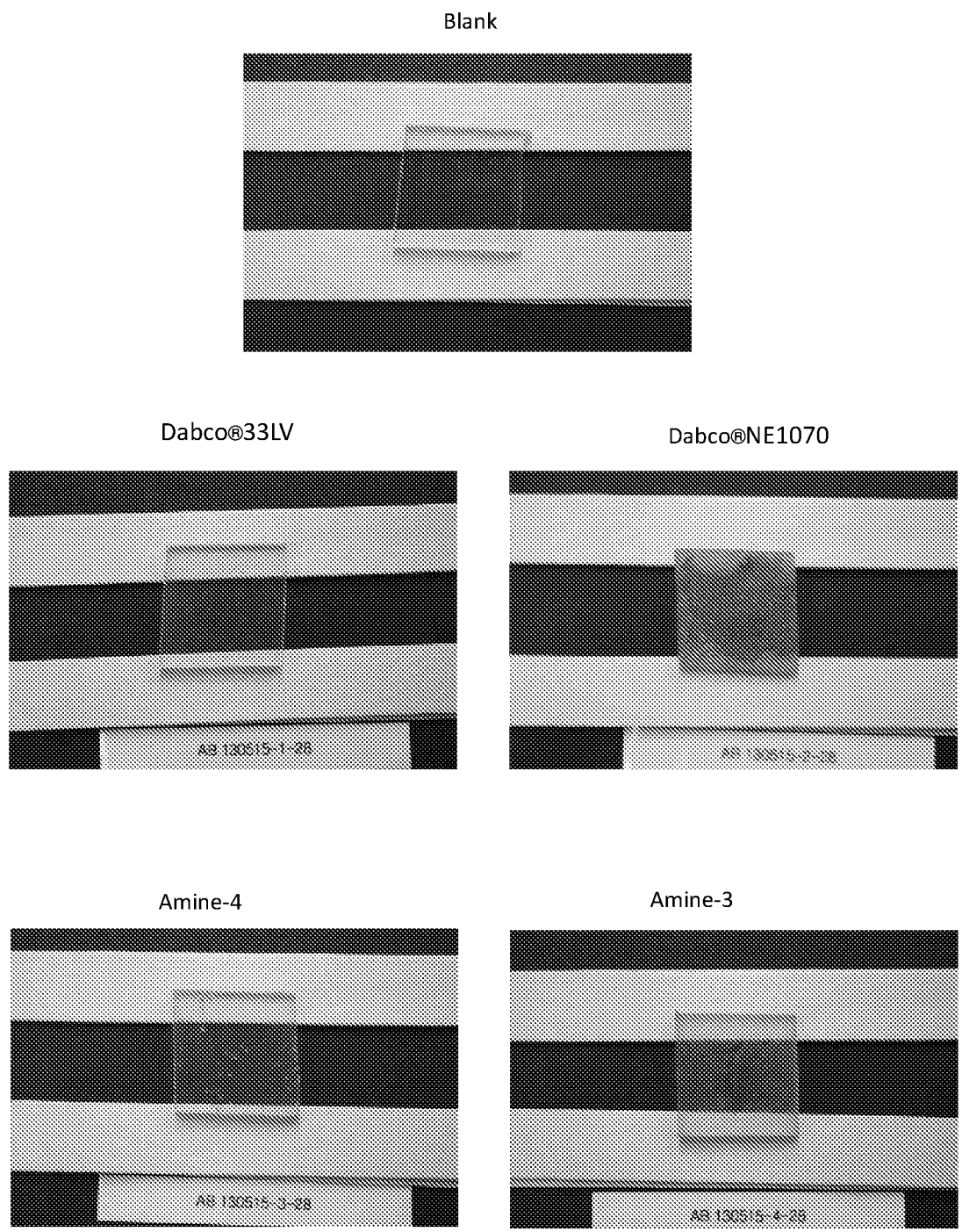
Figure 4: Index 90 Polycarbonate Specimens in Contact with Foam

Figure 5: Chamber Where Foam is Humid Aged at 90oC in Contact With Polycarbonate Specimen (Makrolon GP Clear 099 4mm with no anti-UV agent)
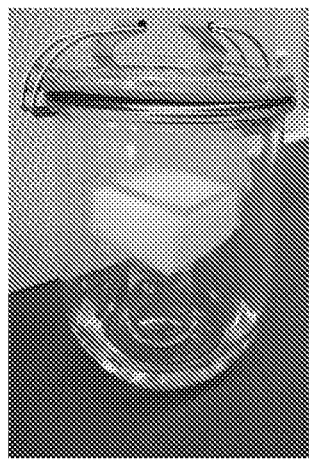

Figure 6
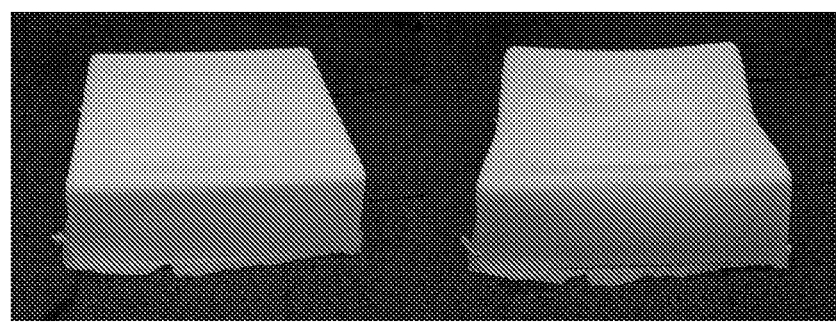
Foam-1 (above)　　　Foam 2 (above)
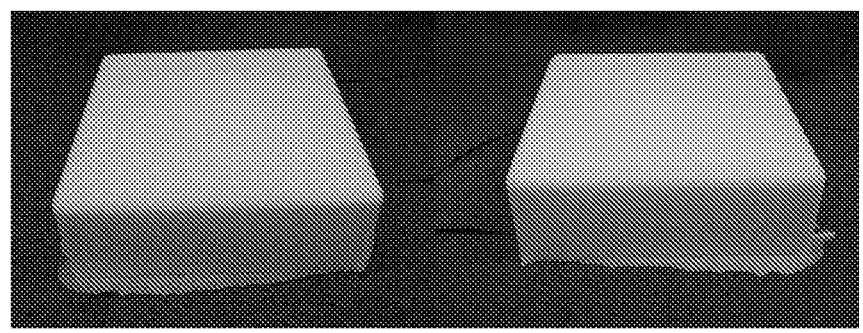
Foam-3 (above)　　　Foam 4 (above)

REACTIVE AMINE CATALYSTS FOR POLYURETHANE APPLICATIONS

This Application is a continuation application of U.S. Ser. No. 15/170,142, filed Jun. 1, 2016, which claims the benefit of Application No. 62/169,046, filed on Jun. 1, 2015, the contents of each of which are hereby incorporated by reference in their entirety into this application.

FIELD OF THE INVENTION

The instant invention relates to tertiary amine catalysts having isocyanate reactive groups that are capable of forming thermally stable covalent bonds and withstanding temperatures of about 120° C. and able to provide polyurethane foam material with good physical properties at various isocyanate indexes.

BACKGROUND OF THE INVENTION

The production of open cell flexible polyurethane foam employs a variety of additives and each one of them plays a role in determining the final characteristics and physical properties of the product. Although these additives represent a small percentage in the overall formulation and their emissions are expected to be relatively low, the increasing demand for low volatile organic contents (VOC's) in finished products has placed additional requirements on additives to achieve these lower emissions while maintaining foam performance.

It is well known that conventional manufacturing procedures to make polyurethane foams use additives that are emissive. One of the strategies used to reduce emissions from foam is based on introducing functional groups on tertiary amine catalysts able to react with isocyanate. Using this approach, the tertiary amine catalysts would remain covalently bonded to the polyurethane polymer preventing its release into the environment. This approach can have some limitations because: a) the functionalized tertiary amine can react with isocyanate prematurely causing undesired side effects such as polymer chain termination which would result in poor physical properties, b) excessive cell opening or foam collapse or excessive cross linking which can result in extensive shrinkage and poor dimensional stability, c) poor physical properties particularly when measured after accelerated thermal humid ageing due to the catalyst remaining in contact with the polyurethane material causing its degradation, d) poor physical properties because the amine catalyst gets immobilized prematurely in the polyurethane polymer being unable to fully finish the curing process, and e) relatively high use levels of catalysts are required due to amine irreversible immobilization in the polyurethane polymer.

Another alternative approach to reduce odor and emissions is based on utilizing materials with increasing molecular weight and/or polarity. However, the limitation of this approach is the required higher use level of the catalyst due to the lower catalytic efficiency due to molecular mobility.

Products such as dimethylaminopropyl urea, bis(dimethylaminopropyl) urea, bis(dimethylaminopropyl) amine and N,N-bis(dimethylaminopropyl)-N-(2-hydroxypropyl) amine can provide acceptable ambient physical properties as compared to industry standards whereas most conventional reactive catalysts cannot always achieve today's consumer and manufacturer requirements. Using these catalysts can reduce significantly the overall emissions from foam. However, ppm levels of amine catalysts can still be detected in finished articles when emissions are measured according to VDA 278 detection method.

One key feature required for the isocyanate reactive tertiary amine catalyst relates to its ability to form a thermally stable covalent bond with the growing polyurethane polymer. The covalent bond should be stable enough to retain the amine catalyst in the polyurethane polymer when foam sample is heated and emissions are removed from the heated chamber by the constant flow of inert gas. Currently, there are a wide variety of functionalized amine polyurethane catalysts capable of reacting with isocyante during the polymerization process. However, in some cases foam produced with some of these reactive catalysts can still have amine emissions because the covalent chemical bonds that holds the amine catalysts into the polyurethane polymer are not sufficiently stable at the temperature of the test. Also, in some other cases foam produced with reactive amine catalysts do not have amine emissions because the covalent chemical bonds that holds the amine catalysts into the polyurethane polymer are sufficiently stable at the temperature of the test but the amine is too reactive towards the isocyanate group leaving the catalyst immobilized early on in the polymerization process with the net result that the finish polyurethane product has poor physical properties or it might partially meet certain physical properties while failing others.

Without wishing to be bound by any theory or explanation, it is believed that such emissions could result either in the release of the amine catalysts from the polyurethane polymer or in the release of by-products and chemical fragments from the thermal decomposition of the amine-polymer adduct.

In addition to thermal stability, these catalysts preferably form hydrolytically stable covalent bonds under a wide variety of conditions and pHs. Hydrolytic stability of the chemical bond between the tertiary amine and the polyurethane polymer plays an important role in applications where polyurethane foam is in contact with textiles that can be exposed to moisture and/or water or in applications where foam can directly be exposed to water while in contact with skin. If the hydrolytic stability of the chemical bond between the polymer and the tertiary amine is not sufficient then tertiary amine catalyst can leach from the polyurethane polymer and may allow amines to directly contact skin leading to skin irritation or skin sensitization.

Finally, thermal stability and catalyst immobilization at lower isocyanate index is an additional performance requirement. In addition to thermal stability at typical indexes such as 90-115 new catalyst need to be able to form covalent bonds with polyurethane polymer that have thermal stability and no emissions at indexes as low as 65 and typically higher than 60. This is a requirement that is difficult to meet because at low isocyanate index there is not sufficient NCO groups able to react with all OH groups from polyols and water so the new amine additive needs to be able to provide simultaneously sufficient catalytic activity to provide good quality foam and effectively compete with OH groups from polyols and water to become part of the polyurethane polymer and be retained in the polymer once the polymerization process is completed. U.S. Pat. No. 5,859,079 disclosed a polyurethane catalyst composition that comprises N,N'-bis(3-dimethylaminopropyl)urea and 3-dimethylaminopropylurea. However when a cured polymer is heated to temperatures as high as 1200° C. amine emissions occur. In addition, water contacting foam produced using this catalyst can have an increased alkalinity. U.S. Pat. No. 6,858,654 discloses a catalyst composition for promoting the polyurethane forming reaction which includes a gelling catalysts and a blowing catalyst. The gelling catalyst are selected from tertiary aminoalkyl substituted primary or secondary amines and the blowing catalysts are selected from bis (aminoalkyl)ethers comprising alkanol moieties, primary amine moieties, or ureido moieties derived from such primary amine moieties. Foams produced with this catalyst are able to provide finished products with no amine emissions, however they cannot meet all physical property requirements.

U.S. Pat. No. 4,101,470 discloses compounds having a OH group able to react and form a covalent bond with isocyanate. An example of such a compound can be obtained when reacting bis(dimethylaminopropyl)amine with propylene oxide to yield bis(3-dimethylaminopropyl)(2-hydroxypropyl)amine. One limitation of the composition is lack of thermal stability of the chemical bond as illustrated in the examples shown in U.S. Pat. No. 6,858,654 where 190 ppm decomposition products from bis-(3-dimethylaminopropyl) (2-hydroxypropyl)amine is observed when foam is heated to 120° C. during testing according to VDA278 emissions test method.

U.S. Pat. No. 4,049,591 claims a method for producing a polyurethane foam which comprises reacting an organic polyisocyanate with an organic polyester polyol or polyether polyol in the presence of a catalytic amount of a compound having a general formula [R"R"N—(CH$_2$)$_3$—]$_2$NCH$_2$CHRY where R" is a lower alkyl, R is hydrogen or lower alkyl and Y is selected from the groups consisting of CN, CONH$_2$, CO$_2$R', CONR$_2$' and COR' where R' is independently H, lower alkyl or aryl. Limitations of these compounds includes emissions due to the lack of functionality able to react with NCO or inability to form thermally stable covalent bonds as well as hydrolytic instability.

The disclosure of the previously identified patents is hereby incorporated by reference.

There is a need in this art for foam made with polyurethane catalyst wherein the resultant foam passes emissions tests, One example of an important emission test is called VDA278. This test requires direct desorption (using heat and a flow of inert gas) of a representative mass of sample (PU foam). Volatile and semi-volatile organic compounds are extracted from the sample into the gas stream and are then re-focused onto a secondary trap prior to injection into a GC (MS) for analysis. VDA278 comprises two extraction stages; 1) VOC-analysis: this involves desorbing the sample at 90° C. for 30 minutes to extract volatile organic compounds and analyzing the emissions by GCMS up to a retention time provided by n-C$_{20}$ aliphatic hydrocarbon standard. This is followed by semi-quantitative analysis of each compound as μg toluene equivalents per gram of sample and 2) FOG-analysis: this involves further desorbing the same sample to 120° C. for 60 minutes to extract semi-volatile organic compounds and analyzing the emissions by GCMS at a retention time interval provided by n-C$_{16}$ to n-C$_{32}$ aliphatic hydrocarbon standards. This is also followed by semi-quantitative analysis of each compound as μg n-hexadecane equivalents per gram of sample. More recently the VDA278 analysis was modified as to utilize in VOC-analysis n-C$_{26}$ aliphatic hydrocarbon standard so as to extend the GCMS retention time range to ensure higher scrutiny of emissions. Similarly, the FOG-analysis was also modified by utilizing n-C$_{14}$ to n-C$_{32}$ aliphatic hydrocarbon standards as to expand the window for monitoring emissions. Thus, catalysts that were previously known as non-emissive or able to pass VDA278 do not necessarily pass the new revisions to the method. Thus, there is also a need in this art for catalysts that react with isocyanates and form thermally stable covalent bonds that are able to withstand the testing conditions that reflect extreme environmental conditions. Such a need can become a challenge as the isocyanate index is reduced to low levels (Index as low as 65 however higher than 60) because there is stoichiometrically an insufficient amount of NCO to react with all OH from polyol and water. In some cases, highly reactive amines will pass the emissions tests but fail on providing some key physical property performance while in other cases less reactive amines will fail emissions test while meeting physical properties. In addition, the needed catalysts should be able to form hydrolytically stable covalent chemical bonds to prevent leaching of amine catalyst from the polyurethane article to avoid amine exposure to end users (e.g., when foam gets directly or indirectly in contact with humidity/moisture and heat). Moreover, the covalent bonds between tertiary amine catalysts and polyurethane polymer should be stable under extreme environmental conditions of heat and humidity such that in the event a polyurethane contacts other materials (for example polycarbonate in contact with polyurethane) the other materials are not damaged or deteriorated.

BRIEF SUMMARY OF THE INVENTION

There is a need in this art for foam manufacturing additives with no amine emissions that can perform as well as the conventional emissive catalysts. The instant invention solves problems associated with conventional reactive catalysts and methods to reduce the amine emissions and in turn overall emissions from open cell flexible polyurethane foam. The instant invention also solves problems associated with catalyst leaching from foam during water contact and thereby avoiding the exposure of end users to amines. The invention further solves problems of material deterioration when certain materials are in contact with polyurethane polymer (e.g., discoloration, staining, among other problems that can be caused by catalyst migration from polyurethane foam during extreme environmental conditions of heat and humidity). The invention solves these problems while providing foam products with optimum physical properties and foam rate or rise kinetics.

The instant invention employs at least one high molecular weight (MW) tertiary amine gelling catalyst having at least a secondary OH functionality functionality and/or at least one urea functionality in its structure. The MW can range from about 300 to about 3000, about 300 to about 2000 and in some cases about 300 to about 1000.

In one aspect of the invention, the inventive gelling amine catalyst comprises a tertiary amine compound with the general formula A-NR$^1$R$^2$ with A=[Me$_2$N—(CH$_2$)$_3$]$_2$N—(CH$_2$)$_3$— and R$^1$=R$^2$=—CH$_2$—CH(R$^3$)OH or R$^1$=H and R$^2$=—CH$_2$—CH(R$^3$)OH with R$^3$=H, C$_1$-C$_6$ or A=[Me$_2$N—(CH$_2$)$_3$]$_2$N—(CH$_2$)$_3$— and R$^1$=H and R$^2$=—CO—NH-A or R$^1$=H and R$^2$=—CO—NH$_2$.

The inventive gelling amine catalyst can provide the following benefits: a) elimination of emissions originating from the amine catalysts under rigorous conditions of temperature at about 120° C.; b) formation of polyurethane polymers wherein the amine catalyst is retained in the polymer when exposed to humidity or water at various temperatures and pHs; c) minimal or no deterioration of other materials such as polycarbonate that come into contact with polyurethane polymer made with the catalyst of the invention; d) overall emission reduction on VOC and FOG when using the catalyst according to the invention; and e) significant reduction in use level of tertiary amine catalyst due to its high activity despite its high MW.

One aspect of the instant invention relates to using the inventive amine catalysts to produce polyurethane foam having the following desirable characteristics: a) low chemical emissions over a wide range of environmental conditions and isocyanate indexes (e.g., indexes as low as about 65 but higher than about 60); b) sufficient hydrolytic stability to maintain the catalyst covalently bound to foam without leaching of tertiary amine catalyst when foam is exposed to water or aqueous solutions even at temperatures higher than ambient (e.g., temperature range about 25° C. to about 90° C.); and c) stable contact interface between the polyurethane polymer and other polymers (for example polycarbonate) with minimal migration of tertiary amine catalyst from polyurethane polymer to other polymers yielding no noticeable polymer deterioration at the point of contact even under conditions of heat and humidity.

When using the catalyst of the invention to produce a polyurethane foam, the foam produced is characterized by: a) low to no amine emissions and reduced overall emissions as measured by the VDA 278 method; b) excellent physical properties such as tensile and tear strengths, compressions sets, ILDs, support factor and resilience; c) minimal or no deterioration of other materials such as polycarbonate that are in contact with polyurethane polymer; d) amines retained in polyurethane polymer by virtue of strong and thermally stable covalent bonds at about 120° C.; e) sufficient hydrolytic stability that allows tertiary amine to be retained in polyurethane polymer when exposed to moisture or water at various temperatures and pHs; and f) significant reduction in gelling amine catalyst use level due to its high catalytic activity.

In one aspect of the invention, the amine catalyst of the invention can be used in combination with certain amine blowing catalysts such as at least one member selected from the group consisting of N,N,N'-trimethyl-N'-3-aminopropyl-bis(aminoethyl) ether or 2-[N-(dimethylaminoethoxyethyl)-N-methylamino]ethanol. Especially desirable results have been obtained by using N,N,N'-trimethyl-N'-3-aminopropyl-bis(aminoethyl) ether.

Further aspect of the invention relates to a process for making polyurethane foams by using the inventive catalyst and to the resultant foams.

One aspect of the invention relates to a method for making a catalyst comprising contacting acrylonitrile and bis(dimethylaminopropyl)amine under conditions sufficient to obtain bis(dimethylaminopropyl)-cyanoethyl-amine; and contacting bis(dimethylaminopropyl)-cyanoethyl-amine with hydrogen under conditions sufficient to obtain N,N-bis(dimethylaminopropyl)-N-(3-aminopropyl)-amine which is subsequently reacted with an alkylene oxide such as ethylene oxide or propylene oxide or alternatively reacted with urea to give the corresponding mono- and bis-substituted ureas.

Another aspect of the invention relates to a method for making a polyurethane foam comprising contacting at least one polyol and at least one polyisocyanate in the presence of a catalyst comprising a tertiary amine with the general formula $A-NR^1R^2$ with $A=[Me_2N-(CH_2)_3]_2N-(CH_2)_3-$ and $R^1=R^2=-CH_2-CH(R^3)OH$ or $R^1=H$ and $R^2=-CH_2-CH(R^3)OH$ with $R^3=H$, $C_1-C_6$ or $A=[Me_2N-(CH_2)_3]_2N-(CH_2)_3-$ and $R^1=H$ and $R^2=-CO-NH-A$ or $R^1=H$ and $R^2=-CO-NH_2$.

Another aspect of the invention relates to a foam produced in accordance with any of the foregoing aspects wherein the foam is free from amine emissions when measured in accordance with VDA 278.

One aspect of the invention relates to a catalyst composition comprising at least one compound with the general formula $A-NR^1R^2$ with $A=[Me_2N-(CH_2)_3]_2N-(CH_2)_3-$ and $R^1=R^2=-CH_2-CH(R^3)OH$ or $R^1=H$ and $R^2=-CH_2-CH(R^3)OH$ with $R^3=H$, $C_1-C_6$ or $A=[Me_2N-(CH_2)_3]_2N-(CH_2)_3-$ and $R^1=H$ and $R^2=-CO-NH-A$ or $R^1=H$ and $R^2=-CO-NH_2$.

One aspect of the invention relates to the foregoing aspects wherein the compound comprises at least one member selected from the group consisting of N,N'-bis[bis-N",N"-(3-dimethylaminopropyl)-N"-(3-aminopropyl)]urea; N,N-bis(3-dimethylaminopropyl)-N-(3-aminopropyl)] urea; N,N-bis(3-dimethylaminopropyl)-N-(bis(2-hydroxypropyl)-3-aminopropyl)]amine; N,N-bis(3-dimethylaminopropyl)-N—[N',N'-bis(2-hydroxypropyl)-3-aminopropyl]amine; and N,N-bis(3-dimethylaminopropyl)-N-[(2-hydroxypropyl)-3-aminopropyl]amine.

Another aspect of the invention relates to any of the foregoing aspects and further comprising at least one blowing catalyst.

Another aspect of the invention relates to any of the foregoing aspects wherein the blowing catalyst comprises at least one member selected from the group consisting of N,N,N'-trimethyl-N'-3-aminopropyl-bis(aminoethyl) ether or 2-[N-(dimethylaminoethoxyethyl)-N-methylamino]ethanol and N,N,N'-trimethyl-N'-3-aminopropyl-bis(aminoethyl) ether.

One aspect of the invention relates to a composition comprising at least one polyol and at least one gelling catalyst having at least functionality selected from the group consisting of a secondary OH functionality functionality and urea functionality.

Another aspect of the invention relates to using any of the foregoing aspects in a method comprising contacting acrylonitrile and bis(dimethylaminopropyl)amine under conditions sufficient to obtain bis(dimethylaminopropyl)-cyanoethyl-amine; and contacting bis(dimethylaminopropyl)-cyanoethyl-amine with hydrogen under conditions sufficient to obtain N,N-bis(dimethylaminopropyl)-N-(3-aminopropyl)-amine and reacting N,N-bis(dimethylaminopropyl)-N-(3-aminopropyl)-amine under conditions sufficient to produce a compound having urea functionality.

One aspect of the invention relates to the foregoing method wherein N,N-bis(dimethylaminopropyl)-N-(3-aminopropyl)-amine is reacted with at least one member selected from the group consisting of ethylene oxide and propylene oxide.

One aspect of the invention relates to the foregoing methods wherein N,N-bis(dimethylaminopropyl)-N-(3-aminopropyl)-amine is reacted with urea.

Another aspect of the invention relates to a method for making a polyurethane foam comprising contacting at least one polyol and at least one isocyanate in the presence of at least one of the foregoing gelling catalysts, and at least one of the foregoing blowing catalysts.

Another aspect of the invention relates to a method for making a polyurethane foam comprising combining at least one polyol, at least one of the foregoing gelling catalysts and at least one of the foregoing blowing catalyst, and reacting the combination with at least one isocyante.

Another aspect of the invention relates to a foam produced in accordance with any of the foregoing methods or using any of the foregoing compositions.

One aspect of the invention relates to a foam produced in accordance with any of the foregoing methods or using any of the foregoing compositions wherein the foam complies with VDA 278.

The various aspects of the invention can be used alone or in combinations with each other.

BRIEF SUMMARY OF THE DRAWINGS

FIG. 1 is a photograph of foams with NCO Index 90 contacted with polycarbonate surfaces in accordance with Example 8.

FIG. 2 is a photograph of foams with NCO Index 90 contacted with polycarbonate surfaces in accordance with Example 8.

FIG. 3 is a photograph of foams with NCO Index 65 contacted with polycarbonate surfaces in accordance with Example 8.

FIG. 4 is a photograph of foams with NCO Index 90 contacted with polycarbonate surfaces in accordance with Example 8.

FIG. 5 is a photograph of the testing assembly that was used in Example 8.

FIG. 6 is a photograph of foams produced in accordance with Example 11.

DETAILED DESCRIPTION OF THE INVENTION

The instant invention relates to amine catalyst compositions, and methods for making the composition and using the catalyst as a gelling catalyst to make polyurethane foam. The inventive catalyst can be used to: a) minimize foam emissions without compromising foam physical properties; b) provide foam that are hydrolytically stable with no increase in pH on the aqueous phase when foam are exposed to water or moisture under various extreme environmental conditions; c) no damage to materials in contact to polyurethane as a result of catalyst not migrating out of the polyurethane polymer (for example when polycarbonate surfaces are exposed to polyurethane foam under various extreme conditions of temperature and humidity); d) optimum physical properties such as target density (ASTM 3574-A), air flow (ASTM 3574-G), ILDs (indentation load deflection method ASTM 3574-B1), support factor (ASTM 3574-B1) and resilience (ASTM 3574-H) and e) significant reduction in gelling amine catalyst use level due to its high catalytic activity.

Flexible molded foams of the invention are characterized by excellent physical properties typically have target density (ASTM 3574-A) with range of about 28 to about 80 kg/m$^3$, air flow (ASTM 3574-G) with range of about 40 to about 120 L/M, ILDs (indentation load deflection method ASTM 3574-B1) with range of about 150 to about 600 N, support factor (ASTM 3574-B1) with range of about 2.5 to about 3.5, preferably about 3, and resilience (ASTM 3574-H) range of about 40 to about 80%. In one aspect of the invention a desirable foam has a Tensile/HA Tensile/Elongation/HA Elongation=DIN 53571—Range of about 80 to about 200%, a 50% Compression Set=ASTM D3574-D—Range of about 1 to about 20%, a HA Compression Set=ASTM D3574-J1 and J2—Range of about 5 to about 15%, and Tear=ASTM D3574-F—Range of about 150 to about 400.

The inventive amine catalyst with the general formula A-NR$^1$R$^2$ with A=[Me$_2$N—(CH$_2$)$_3$]$_2$N—(CH$_2$)$_3$— and R$^1$=R$^2$=—CH$_2$—CH(R$^3$)OH or R$^1$=H and R$^2$=—CH$_2$—CH(R$^3$)OH with R$^3$=H, C$_1$-C$_6$ or A=[Me$_2$N—(CH$_2$)$_3$]$_2$N—(CH$_2$)$_3$— and R$^1$=H and R$^2$=—CO—NH-A or R$^1$=H and R$^2$=—CO—NH$_2$.

Examples of the inventive catalyst comprise at least one member selected from the group consisting of N,N'-bis[bis-N'',N''-(3-dimethylaminopropyl)-N''-(3-aminopropyl)]urea; N,N-bis(3-dimethylaminopropyl)-N-(3-aminopropyl)] urea; N,N-bis(3-dimethylaminopropyl)-N-(bis(2-hydroxypropyl)-3-aminopropyl)]amine; N,N-bis(3-dimethylaminopropyl)-N—[N',N'-bis(2-hydroxypropyl)-3-aminopropyl]amine; N,N-bis(3-dimethylaminopropyl)-N-[(2-hydroxypropyl)-3-aminopropyl]amine.

One aspect of the invention relates to tertiary amine catalysts having the chemical structure A-NR$^1$R$^2$ with A=[Me$_2$N—(CH$_2$)$_3$]$_2$N—(CH$_2$)$_3$— and R$^1$=R$^2$=—CH$_2$—CH(R$^3$)OH or R$^1$=H and R$^2$=—CH$_2$—CH(R$^3$)OH with R$^3$=H, C$_1$-C$_6$ or A=[Me$_2$N—(CH$_2$)$_3$]$_2$N—(CH$_2$)$_3$— and R$^1$=H and R$^2$=—CO—NH-A or R$^1$=H and R$^2$=—CO—NH$_2$ wherein Me is CH$_3$ group. The inventive catalyst can be used in amounts ranging from about 0.1 pphp to about 20 pphp, about 0.1 pphp to about 10 pphp and in some cases about 0.1 pphp to about 5 pphp.

The inventive amine catalyst can be prepared by any suitable method. One suitable method for making the inventive catalyst comprises contacting acrylonitrile and bis(dimethylaminopropyl)amine under conditions sufficient to obtain bis(dimethylaminopropyl)-cyanoethyl-amine; and contacting bis(dimethylaminopropyl)-cyanoethyl-amine with hydrogen under conditions sufficient to obtain N,N-bis(dimethylaminopropyl)-N-(3-aminopropyl)-amine which is subsequently reacted with an alkylene oxide such as ethylene oxide or propylene oxide or alternatively reacted with urea to give the corresponding mono- and bis-substituted ureas. While any suitable method for making the inventive catalyst can be employed, an example of a suitable method comprising making Bis(3-dimethylaminopropyl)-N-(3-aminopropyl)-amine by reacting bis(3-dimethylaminopropyl) amine with acrylonitrile at an approximate molar ratio of 1:1 followed by catalytic hydrogenation using Raney-Cobalt catalyst as described in instant Example 1. Bis(3-dimethylaminopropyl)-N-(3-aminopropyl)-amine can be reacted with an alkylene oxide typically ethylene oxide or propylene oxide in an amine:alkylene oxide molar ratio from 0.2 to 2 and typically 0.5 to 2 and more typically from 1.0 to 2.0. Bis(3-dimethylaminopropyl)-N-(3-aminopropyl)-amine can be reacted with urea in an amine:urea molar ratio from 0.2 to 2 and typically 0.5 to 2 and more typically from 1.0 to 2.0.

In one aspect of the invention, the inventive catalyst can be used in combination with at least one blowing amine catalysts selected from the group consisting of N,N,N'-trimethyl-N'-3-aminopropyl-bis(aminoethyl) ether or 2-[N-(dimethylaminoethoxyethyl)-N-methylamino]ethanol, and typically N,N,N'-trimethyl-N'-3-aminopropyl-bis(aminoethyl) ether. The amount of blowing amine catalyst is typically about 0 pphp to about 5 pphp, about 0.01 pphp to about 2 pphp and in some cases about 0.05 pphp to about 1 pphp. These catalyst can be combined by any suitable method such as adding each separate catalysts to a polyol premix or alternatively premixing both catalysts and adding the mixture of catalysts to the polyol premix.

The instant invention also relates to a process to make low or no amine emissions polyurethane foams using a combination of certain isocyanate reactive tertiary amines gelling catalysts in combination with catalysts of the invention having the chemical structure A-NR$^1$R$^2$ with A=[Me$_2$N—(CH$_2$)$_3$]$_2$N—(CH$_2$)$_3$— and R$^1$=R$^2$=—CH$_2$—CH(R$^3$)OH or R$^1$=H and R$^2$=—CH$_2$—CH(R$^3$)OH with R$^3$=H, C$_1$-C$_6$ or A=[Me$_2$N—(CH$_2$)$_3$]$_2$N—(CH$_2$)$_3$— and R$^1$=H and R$^2$=—CO—NH-A or R$^1$=H and R$^2$=—CO—NH$_2$ wherein Me is CH$_3$ group. The isocyanate reactive gelling tertiary amines catalysts include any of the following functionalities urea, secondary-amine, primary amine, amides or secondary hydroxyl group. The combination of an isocyante-reactive tertiary amine catalyst together with gelling catalyst of the invention produces foam with minimal emissions when compared with foam produced with any sole conventional emissive or non-emissive gelling catalyst described in the prior art. The % ratio of inventive catalyst to the foregoing gelling catalyst is typically about 100% to about 5% about 80% to about 10% and in some cases about 70% to about 20% These catalyst can be combined by any suitable method such as such as adding each separate catalysts to the premix or alternatively premixing both catalysts and adding the mixture of catalysts to the polyol premix.

Preparation of Foams

Foams of any of the various types known in the art may be made using the methods of this invention, using typical polyurethane formulations to which have been added the appropriate amount of tertiary amine catalysts having the chemical structure A-NR$^1$R2 with A=[Me$_2$N—(CH$_2$)$_3$]$_2$N—(CH$_2$)$_3$— and R$^1$=R$^2$=—CH$_2$—CH(R$^3$)OH or R$^1$=H and R$^2$=—CH$_2$—CH(R$^3$)OH with R$^3$=H, C$_1$-C$_6$ or A=[Me$_2$N—(CH$_2$)$_3$]$_2$N—(CH$_2$)$_3$— and R$^1$=H and R$^2$=—CO—NH-A or R$^1$=H and R$^2$=—CO—NH$_2$ wherein Me is CH$_3$ group. For example, flexible polyurethane foams with the excellent characteristics described herein will typically comprise the components shown below in Table I, in the amounts indicated. The components shown in Table 1 will be discussed in detail later below.

TABLE 1

Polyurethane Components

| Component | Parts by Weight |
|---|---|
| Base Polyol | 20-100 |
| Polymer polyol | 0-80 |
| Silicone surfactant | 0.5-10 |
| Blowing agent | 2-4.5 |
| Crosslinker | 0.5-2 |
| Catalyst | 0.25-10 |
| Carboxylic acid (optional) | 0.05-3.0 |
| Polyisocyanate | To provide NCO index = 60-115 |

The amount of polyisocyanate used in polyurethane formulations according to the invention is not limited, but it will typically be within those ranges known to those of skill in the art. An exemplary range is given in table I, indicated by reference to "NCO Index" (isocyanate index). As is known in the art, the NCO index is defined as the number of equivalents of isocyanate, divided by the total number of equivalents of active hydrogen, multiplied by 100. The NCO index is represented by the following formula.

NCO index=[NC0/(OH+NH)]*100

Flexible foams typically use copolymer polyols as part of the overall polyol content in the foam composition, along with base polyols of about 4000-5000 weight average molecular weight and hydroxyl number of about 28-35. Base polyols and copolymer polyols will be described in detail later herein.

The polyols can have a functionality of about 2 to about 8, about 2 to about 6 and in some cases about 2 to about 4. The polyols can also have a hydroxyl number from about 10 to about 900, and typically about 15 to about 600 and more typically about 20 to about 200.

Catalysts

The catalysts of the present invention being tertiary amine catalysts having the chemical structure A-NR$^1$R$^2$ with A=[Me$_2$N—(CH$_2$)$_3$]$_2$N—(CH$_2$)$_3$— and R$^1$=R$^2$=—CH$_2$—CH(R$^3$)OH or R$^1$=H and R$^2$=—CH$_2$—CH(R$^3$)OH with R$^3$=H, C$_1$-C$_6$ or A=[Me$_2$N—(CH$_2$)$_3$]$_2$N—(CH$_2$)$_3$— and R$^1$=H and R$^2$=—CO—NH-A or R$^1$=H and R$^2$=—CO—NH$_2$ wherein Me is CH$_3$ group can be used as the sole gelling catalyst but alternatively the inventive catalysts can be used in combination with other tertiary amines containing isocyante reactive groups. Isocyanate reactive groups present in the alternative tertiary amine gelling co-catalyst consist essentially of primary amine, secondary amine, primary-hydroxyl group, secondary-hydroxyl group, amide and urea. Examples of such gelling co-catalysts comprise at least one member selected from the group consisting of N,N-bis(3-dimethylaminopropyl)-N-(2-hydroxypropyl) amine; N,N-dimethyl-N',N'-bis(2-hydroxypropyl)-1,3-propylenediamine; dimethylaminopropylamine (DMAPA); N-methyl-N-2-hydroxypropylpiperazine, bis-dimethylaminopropyl amine (POLYCAT® 15), dimethylaminopropyl urea and N,N'-bis(3-dimethylaminopropyl) urea (DABCO@NE1060, DABCO® NE1070, DABCO@ NE1080 and DABCO® NE1082), 1,3-bis(dimethylamino)-2-propanol, 6-dimethylamino-1-hexanol, N-(3-aminopropyl)imidazole, N-(2-hydroxypropyl)imidazole, N,N'-bis(2-hydroxypropyl) piperazine, N-(2-hydroxypropyl)-morpholine, and N-(2-hydroxyethylimidazole). The amount of the inventive catalyst can range from about 0.01 pphp to about 20 pphp about 0.05 pphp to about 10 pphp and in some cases about 0.1 pphp to about 5 pphp. The amount of gelling co-catalyst can range from about 0 pphp to about 19 pphp, about 0 pphp to about 15 ppm and in some cases about 0 pphp to about 10 pphp. Examples of blowing co-catalysts containing isocyanate reactive groups that can be used in combination with the above mentioned gelling catalysts include 2-[N-(dimethylaminoethoxyethyl)-N-methylamino] ethanol (DABCO® NE200), and N,N,N'-trimethyl-N'-3-aminopropyl-bis(aminoethyl) ether (DABCO® NE300). The amount of blowing co-catalyst can range from about 0 pphp to about 5 pphp, about 0.01 pphp to about 2 pphp and in some cases about 0.05 to about 1 pphp.

The catalyst compositions may also include other components, for example transition metal catalysts such as organotin compounds or bismuth carboxylates for example when the desired polyurethane foam is a flexible slab stock. Metal catalyst can also comprise at least one member selected from the group consisting of dialkyltin carboxylates such as dibutylin dilaureate, dimethyltin dilaureate, dimethyltin diacetate, dibutyltin diacetate, dimethyltin dilaurylmercaptide, dibutyltin dilaurylmercaptide, dimethyltin diisooctylmaleate, dibutyltin diisooctylmaleate, dimethyltin bi(2-thylhexyl mercaptacetate), dibutyltin bi(2-thylhexyl mercaptacetate), dimethyltinneodecanoate, dibutyltinneodecanoate, dimethyltinisononanoate, dibutyltinisononanoate, stannous octoate, stannous neodecanoate, stannous isononanoate or other suitable organotin catalysts or other suitable stannous carboxylate salts or a combination thereof. Other metals and salts thereof can also be included, such as, for example, bismuth (Bi). Suitable metal salts include carboxylate salts including salts of acetic acid, propanoic acid, butanoic acid, pentanoic acid, neopentanoic acid, hexanoic acid, 2-ethylhexyl carboxylic acid, neohexanoic acid, octanoic acid, neooctanoic acid, heptanoic acid, neoheptanoic acid, nonanoic acid, neononanoic acid, decanoic acid, neodecanoic acid, undecanoic acid, neoundecanoic acid, dodecanoic acid, neododecanoic acid, myristic acid, pentadecanoic acid, hexadecanoic acid, heptadecanoic acid, octadecanoic acid and other suitable carboxylic acids. Other salts of transition metals of lead (Pb), iron (Fe), zinc (Zn) with pentanoic acid, neopentanoic acid, hexanoic acid, 2-ethylhexyl carboxylic acid, octanoic acid, neooctanoic acid, neoheptanoic acid, neodecanoic acid, neoundecanoic acid, neododecanoic acid, and other suitable carboxylic acids may also be included. The amount of the foregoing metal catalyst can range from about 0 pphp to about 20 pphp, about 0 pphp to about 10 pphp and in some cases about 0 pphp to about 0.01 pphp.

The inventive catalyst (and if desired co-gelling and blowing catalysts) can also be acid blocked with an acid including carboxylic acids (alkyl, substituted alkyl, alkylene, aromatic, substituted aromatic) sulfonic acids or any other organic or inorganic acid. Examples of carboxylic acids include mono-acids, di-acids or poly-acids with or without isocyanate reactive groups. Examples of carboxylic acids include formic acid, acetic acid, propionic acid, butanoic acid, pentanoic acid, neopentanoic acid, hexanoic acid, 2-ethylhexyl carboxylic acid, neohexanoic acid, octanoic acid, neooctanoic acid, heptanoic acid, neoheptanoic acid, nonanoic acid, neononanoic acid, decanoic acid, neodecanoic acid, undecanoic acid, neoundecanoic acid, dodecanoic acid, neododecanoic acid, myristic acid, pentadecanoic acid, hexadecanoic acid, heptadecanoic acid, octadecanoic acid, benzoic acid, oxalic acid, malonic acid, succinic acid, glutaric acid, adipic acid, pimelic acid, suberic acid, azelaic acid, sebacic acid, glycolic acid, lactic acid, tartaric acid, citric acid, malic acid, salicylic acid and the like.

While the inventive amine catalyst of the invention can be used with amines listed above, such usage can increase emissions from foam during the foam's useful lifetime as well as during foam manufacturing because the thermal stability of the chemical bonds between the isocyanate reactive co-catalysts are not as stable as the inventive catalyst. Typically, the total loading of the tertiary amine catalyst(s) (i.e., inventive plus any co-gelling catalysts) for making foam according to the invention will be in the range of about 0.1 to about 20 pphp, more typically about 0.1 to about 10 pphp, and most typically about 0.1 to about 5 pphp. However, any effective amount may be used. The term "pphp" means parts per hundred parts polyol.

Organic Isocyanates

Suitable organic isocyanate compounds include, but are not limited to, hexamethylene diisocyanate (HDI), phenylene diisocyanate (PDI), toluene diisocyanate (TDI), and 4,4'-diphenylmethane diisocyanate (MDI). In one aspect of the invention, 2,4-TDI, 2,6-TDI, or any mixture thereof is used to produce polyurethane foams. Other suitable isocyanate compounds are diisocyanate mixtures known commercially as "crude MDI." One example is marketed by Dow Chemical Company under the name PAPI, and contains about 60% of 4,4'-diphenylmethane diisocyanate along with other isomeric and analogous higher polyisocyanates. While any suitable isocyanate can be used, an example of such comprises isocyanate having an index range from about 60 to about 200 and typically from about 90 to about 120. The amount of isocyanate typically ranges from about 95 to about 105 and in one aspect of the invention the iscyanate index ranges from about 60 to about 65.

Polyol Component

Polyurethanes are produced by the reaction of organic isocyanates with the hydroxyl groups of polyol, typically a mixture of polyols. The polyol component of the reaction mixture includes at least a main or "base" polyol. Base polyols suitable for use in the invention include, as non-limiting examples, polyether polyols. Polyether polyols include poly(alkylene oxide) polymers such as poly(ethylene oxide) and poly(propylene oxide) polymers and copolymers with terminal hydroxyl groups derived from polyhydric compounds, including diols, triols and higher alcohols. Examples of diols and triols for reaction with the ethylene oxide or propylene oxide include ethylene glycol, propylene glycol, 1,3-butanediol, 1,4-butanediol, 1,6-hexanediol, neopentyl glycol, diethylene glycol, dipropylene glycol, pentaerythritol, glycerol, diglycerol, trimethylol propane, and similar low molecular weight polyols. Other base polyol examples known in the art include polyhydroxy-terminated acetal resins, hydroxyl-terminated amines and hydroxyl-terminated polyamines. Examples of these and other suitable isocyanate-reactive materials may be found in U.S. Pat. No. 4,394,491; hereby incorporated by reference. Suitable polyether polyols also include those containing tertiary amine groups than can catalyze the gelling and the blowing reaction of polyurethanes, for example those described in U.S. Pat. No. 8,367,870; WO 03/016373 A1; WO 01/58976 A1; W02004/060956 A1; W003/016372 A1; and W003/055930 A1; the disclosure of the foregoing US and WO publications is hereby incorporated by reference. Other useful polyols may include polyalkylene carbonate-based polyols and polyphosphate-based polyols.

In one aspect of the invention, a single high molecular weight polyether polyol may be used as the base polyol. Alternatively, a mixture of high molecular weight polyether polyols, for example, mixtures of di- and tri-functional materials and/or different molecular weight or different chemical composition materials may be used. Such di- and tri-functional materials include, but are not limited to polyethylene glycol, polypropylene glycol, glycerol-based polyether triols, trim ethylolpropane-based polyether triols, and other similar compounds or mixtures.

In addition to the base polyols described above, or instead of them, materials commonly referred to as "copolymer polyols" may be included in a polyol component for use according to the invention. Copolymer polyols may be used in polyurethane foams to increase the resistance to deformation, for example to improve the load-bearing properties. Depending upon the load-bearing requirements, copolymer polyols may comprise from about 0 to about 80 percent by weight of the total polyol content.

Examples of copolymer polyols include, but are not limited to, graft polyols and polyuria modified polyols, both of which are known in the art and are commercially available.

Graft polyols are prepared by copolymerizing vinyl monomers, typically styrene and acrylonitrile, in a starting polyol. The starting polyol is typically a glycerol-initiated triol, and is typically end-capped with ethylene oxide (approximately 80-85% primary hydroxyl groups). Some of the copolymer grafts to some of the starting polyol. The graft polyol also contains homopolymers of styrene and acrylonitrile and unaltered startingpolyol. The styrene/acrylonitrile solids content of the graft polyol typically ranges from 5 wt % to 45 wt %, but any kind of graft polyol known in the art may be used.

Polyurea modified polyols are formed by the reaction of a diamine and a diisocyanate in the presence of a starting polyol, with the product containing polyurea dispersion. A variant of polyurea modified polyols, also suitable for use, are polyisocyanate poly addition (PIPA) polyols, which are formed by the in situ reaction of an isocyanate and an alkanolamine in a polyol.

Other suitable polyols that can be used according to the invention include natural oil polyols or polyols obtained from renewable natural resources such as vegetable oils. Polyols useful in the preparation of polyurethane foam from inexpensive and renewable resources are highly desirable to minimize the depletion of fossil fuel and other non-sustainable resources. Natural oils consist of triglycerides of saturated and unsaturated fatty acids. One natural oil polyol is castor oil, a natural triglyceride of ricinoleic acid which is commonly used to make polyurethane foam even though it has certain limitations such as low hydroxyl content. Other natural oils need to be chemically modified to introduce sufficient hydroxyl content to make them useful in the production of polyurethane polymers. There are two chemically reactive sites that can be considered when attempting to modify natural oil or fat into a useful polyol: 1) the unsaturated sites (double bonds); and 2) the ester functionality. Unsaturated sites present in oil or fat can be hydroxylated via epoxidation followed by ring opening or hydroformilation followed by hydrogenation. Alternatively, trans-esterification can also be utilized to introduce OH groups in natural oil and fat. The chemical process for the preparation of natural polyols using epoxidation route involves a reaction mixture that requires epoxidized natural oil, a ring opening acid catalyst and a ring opener. Epoxidized natural oils include epoxidized plant-based oils (epoxidized vegetable oils) and epoxidized animal fats. The epoxidized natural oils may be fully or partially epoxidized and these oils include soybean oil, corn oil, sunflower oil, olive oil, canola oil, sesame oil, palm oil, rapeseed oil, tung oil, cotton seed oil, safflower oil, peanut oil, linseed oil and combinations thereof. Animal fats include fish, tallow and lard. These natural oils are triglycerides of fatty acids which may be saturated or unsaturated with various chain lengths from $C_{12}$ to $C_{24}$. These acids can be: 1) saturated: lauric, myristic, palmitic, steric, arachidic and lignoceric; 2) monounsaturated: palmitoleic, oleic, 3) poly-unsaturated: linoleic, linolenic, arachidonic. Partially or fully epoxidized natural oil may be prepared when reacting peroxyacids under suitable reaction conditions. Examples of peroxyacids utilized in the epoxidation of oils have been described in WO 2006/116456 Al; hereby incorporated by reference. Ring opening of the epoxidized oils with alcohols, water and other compounds having one or multiple nucleophilic groups can be used. Depending on the reaction conditions oligomerization of the epoxidized oil can also occur. Ring opening yields natural oil polyol that can be used for the manufacture of polyurethane products. In the hydroformilation/hydrogenation process, the oil is hydroformylated in a reactor filled with a hydrogen/carbon monoxide mixture in the presence of a suitable catalyst (typically cobalt or rhodium) to form an aldehyde which is hydrogenated in the presence of cobalt or nickel catalyst to form a polyol. Alternatively, polyol from natural oil and fats can be produced by trans-esterification with a suitable poly-hydroxyl containing substance using an alkali metal or alkali earth metal base or salt as a transesterification catalyst. Any natural oil or alternatively any partially hydrogenated oil can be used in the transesterification process. Examples of oils include but are not limited to soybean, corn, cottonseed, peanut, castor, sunflower, canola, rapeseed, safflower, fish, seal, palm, tung, olive oil or any blend. Any multifunctional hydroxyl compound can also be used such as lactose, maltose, raffinose, sucrose, sorbitol, xylitol, erythritol, mannitol, or any combination.

Polyols amounts are defined by pphp. There are 3 types of polyols above defined: standard polyol or polyether polyol which can be used in the range of about 100 pphp (the only polyol) to about 10 pphp. The copolymer polyol (CPP) can be used in the range of about 0 to about 80 pphp. Finally the NOP (natural oil polyol) which typically can be present from about 0 to about 40 pphp.

Polyols can have an OH number from 10 to about 900 and a functionality from about 2 to 8. The polyol OH number and functionality are selected in order to obtain a foam having desired physical properties.

Open cell flexible molded foams typically use a main or "base" polyether polyol. Polyether polyols include poly (alkylene oxide) polymers such as poly(ethylene oxide) and poly(propylene oxide) polymers and copolymers with terminal hydroxyl groups derived from polyhydric compounds, including diols and triols. These polyols can have a functionality of about 2 to about 8, about 2 to about 6 and typically about 2 to about 4. The polyols can also have a hydroxyl number from about 10 to about 900, and typically about 15 to about 600 and more typically about 20 to about 50. Flexible molded foams also use copolymer polyols as part of the overall polyol content in the foam composition with OH numberst typically in the range of 15 to 50, MW ranges typically from 1200 to 8000 and more typically 2000 to 6000 and % solids form 10% to 60%. Open cell low density spray foam typically use a polyether polyol with an average MW from 1500 tp 6000 and OH number from 15 to 50. Polyols amounts are defined by pphp. There are 4 types of polyols above defined: standard polyol or polyether polyol which can be used in the range of about 100 pphp (the only polyol) to about 10 pphp. The copolymer polyol (CPP) can be used in the range of about 0 to about 80 pphp. The NOP (natural oil polyol) can be present from about 0 to about 40 pphp. Finally, the Mannich polyol is used in combination with other polyol and in a range from 0 pphp to 80 pphp, about 0 pphp to about 50 pphp and in some cases about 0 pphp to about 20 pphp.

Blowing Agents

Polyurethane foam production may be aided by the inclusion of a blowing agent (BA) to produce voids in the polyurethane matrix during polymerization. Any suitable blowing agent may be used. Suitable blowing agents include compounds with low boiling points which are vaporized during the exothermic polymerization reaction. Such blowing agents are generally inert or they have low reactivity and therefore it is likely that they will not decompose or react during the polymerization reaction. Examples of low reactivity blowing agents include, but are not limited to, carbon dioxide, chlorofluorocarbons (CFCs), hydrofluorocarbons (HFCs), hydrochlorofluorocarbons (HCFCs), fluoroolefins (FOs), chlorofluoroolefins (CFOs), hydrofluoroolef ins (HFOs), hydrochlorfluoroolefins (HCFOs), acetone, and low-boiling hydrocarbons such as cyclopentane, isopentane, n-pentane, and their mixtures. The amount of BA is typically from about 0 (for example when water is used to blown the polyurethane polymer) to about 80 pphp. Other suitable blowing agents include compounds, for example water, that react with isocyanate compounds to produce a gas. Water (which reacts with isocyanate making $CO_2$) can be present in the range from about 0 (if a BA is included) to about 60 pphp (a very low density foam) and typically from about 1.0 pphp to about 10 pphp and, in some cases, from about 2.0 pphp to about 5 pphp.

Other Optional Components

A variety of other ingredients may be included in the formulations for making foams according to the invention.

Examples of optional components include, but are not limited to, cell stabilizers, crosslinking agents, chain extenders, pigments, fillers, flame retardants, auxiliary urethane gelling catalysts, auxiliary urethane blowing catalysts, transition metal catalysts, alkali and alkali earth carboxylate salts and combinations of any of these.

Cell stabilizers may include, for example, silicone surfactants as well as organic anionic, cationic, zwiterionic or nonionic surfactants. Examples of suitable silicone surfactants include, but are not limited to, polyalkylsiloxanes, polyoxyalkylene polyol modified dimethylpolysiloxanes, alkylene glycol-modified dim ethylpolysiloxanes, or any-combination thereof. Suitable anionic surfactants include, but are not limited to, salts of fatty acids, salts of sulfuric acid esters, salts of phosphoric acid esters, salts of sulfonic acids, and combinations of any of these. Suitable cationic surfactants include, but are not limited to quaternary ammonium salts (pH dependent or permanently charged) such as cetyl trimethylammonium chloride, cetyl pyridinium chloride, polyethoxylated tallow amine, benzalkonium chloride, benzethonium chloride and the like. Suitable zwiterionic or amphoteric surfactants include but are not limited to sultaines, aminoacids, imino acids, betaines and phosphates. Suitable non-ionic surfactants include but are not limited to fatty alcohols, polyoxyethylene glycol alkyl ethers, polyoxypropylene glycol alkyl ethers, glucosides (such as decyl, lauryl and octyl glucosides), polyoxyethylene glycol alkyl phenol ethers, glycol alkyl esters, and the like. Cell stabilizers can used in an amount from about 0.1 to about 20 pphp and typically from about 0.1 to about 10 pphp and, in some cases, from about 0.1 to about 5.0 pphp. Fire retardants can be used in an amount from about 0 to about 20 pphp and from about 0 to about 10 pphp and from about 0 to about 5 pphp.

Crosslinking agents include, but are not limited to, low-molecular weight compounds containing at least two moieties selected from hydroxyl groups, primary amino groups, secondary amino groups, and other active hydrogen-containing groups which are reactive with an isocyanate group. Crosslinking agents include, for example, polyhydric alcohols (especially trihydric alcohols, such as glycerol and trimethylolpropane), polyamines, and combinations thereof. Non-limiting examples of polyamine crosslinking agents include diethyltoluenediamine, chlorodiaminobenzene, diethanolamine, diisopropanolamine, triethanolamine, tripropanolamine, 1,6-hexanediamine, and combinations thereof. Typical diamine crosslinking agents comprise twelve carbon atoms or fewer, more commonly seven or fewer. Crosslinking agents can used in an amount from about 0.1 to about 20 pphp and typically from about 0.1 to about 10 pphp and, in some cases, from about 0.1 to about 5.0 pphp.

Examples of chain extenders include, but are not limited to, compounds having hydroxyl or amino functional group, such as glycols, amines, diols, and water. Specific non-limiting examples of chain extenders include ethylene glycol, diethylene glycol, propylene glycol, dipropylene glycol, 1,4-butanediol, 1,3-butanediol, 1,5-pentanediol, neopentyl glycol, 1,6-hexanediol, 1,10-decanediol, 1,12-dodecanediol, ethoxylated hydroquinone, 1,4-cyclohexanediol, N-methylethanolamine, N-methylisopropanolamine, 4-aminocyclohexanol, 1,2-diaminoethane, 2,4-toluenediamine, or any mixture thereof. Chain extenders can used in an amount from about 0.1 to about 100 pphp and typically from about 0.1 to about 50 pphp and, in some cases, from about 0.1 to about 5.0 pphp.

Pigments may be used to color code the polyurethane foams during manufacture, for example to identify product grade or to conceal yellowing. Pigments may include any suitable organic or inorganic pigments known in the polyurethane art. For example, organic pigments or colorants include, but are not limited to, azo/diazo dyes, phthalocyanines, dioxazines, and carbon black. Examples of inorganic pigments include, but are not limited to, titanium dioxide, iron oxides, or chromium oxide. The amount of pigment can range from about 0 pphp (no pigments added) to about 40 pphp.

Fillers may be used to increase the density and load bearing properties of polyurethane foams. Suitable fillers include, but are not limited to, barium sulfate or calcium carbonate. The amount of fillers can range from about 0 pphp (no fillers added) to about 40 pphp.

Flame retardants may be used to reduce the flammability of polyurethane foams. For example, suitable flame retardants include, but are not limited to, chlorinated phosphate esters, chlorinated paraffins, or melamine powders. Flame retardants can be used in an amount from about 0 to about 20 pphp and from about 0 to about 10 pphp and from about 0 to about 5 pphp.

In one aspect of the invention, the inventive catalyst is free or substantially free of certain amine catalysts. Examples of materials that can be excluded are amine catalysts having no isocyanate groups typically know as fugitive catalysts in particular when their use levels are >0.20 pphp and in some cases >0.10 pphp and in some cases >0.05 pphp as these materials are contributors to amine emissions. A list of examples of fugitive amine catalysts within this category include triethylenediamine (TEDA), N-methylimidazole, 1,2-dimethyl-imidazole, N-methylmorpholine, N-ethylmorpholine, triethylamine, N,N'-dimethyl-piperazine, 1,3,5-tris(dimethylaminopropyl) hexahydrotriazine, 2,4,6-tris(dimethylamino-methyl)phenol, N-methyldicyclohexylamine, pentamethyldipropylene triamine, N-methyl-N'-(2-dimethylamino)-ethyl-piperazine, tributylamine, pentamethyldiethylenetriamine, hexamethyltriethylenetetramine, heptamethyltetraethylenepentamine, dimethylamino-cyclohexylamine, bis(dimethylaminoethyl) ether, tris(3-dimethylamino)propylamine, 1,8-diazabicyclo [5.4.0] undecene, or its acid blocked derivatives, and the like, as well as any mixture thereof.

Certain aspects of the invention are illustrated by the following Examples. These Examples are illustrative only and shall not limit the scope of any claims appended hereto. Foams were evaluated by using Handmix Evaluations or Machine Evaluations as described below.

EXAMPLES

Handmix Evaluations

Handmix experiments were conducted using the following procedure. Formulations were blended together for approximately 10 minutes using a mechanical mixer equipped with a 7.6 cm diameter high shear mixing blade, rotating at 5000 rpm. Premixed formulations were maintained at 23±1° C. using a low temperature incubator. Mondur® TD-80 (an 80/20 2,4/2,6 isomer blend of toluene diisocyanate) or modified MDI was added to the premix at the correct stoichiometric amount for the reported index of each foam. The mixture was blended together with Premier Mill Corporation Series 2000, Model 89, and dispersed for approximately five seconds. The foaming mixture was transferred to an Imperial Bondware #GDR-170 paper bucket and allowed to free rise while data was recorded.

Machine Evaluations

Machine runs for the flexible molded foam were conducted on a Hi Tech Sure Shot MH R-50, cylinder displacement series and high-pressure machine. Fresh premixes, consisting of the appropriate polyols, water, crosslinker, surfactants and catalysts for each formulation were charged to the machine. Mondur® TD-80 or Lupranat® T80 (commercially available isocyanate) was used throughout the entire study. All chemical temperatures were held at 23±2° C. via the machine's internal temperature control units. Foam pours were made into an isothermally controlled, heated aluminum mold maintained at 63±2° C. The mold was a typical physical property tool designed with internal dimensions of 40.6 cm×40.6 cm×10.2 cm. The mold has five vents, each approximately 1.5 mm in diameter, centered in each corner 10.0 cm from each edge and the geometric center of the lid. The mold was sprayed with a solvent-based release agent, prior to every pour and allowed to dry for one minute before pouring. The foam premix was puddle poured into the center of the mold with a wet chemical charge weight capable of completely filling the mold and obtaining the desired core densities reported typically 40 Kg/m$^3$ and 45 Kg/m$^3$. Minimum fill requirements were established for each formulation evaluated. The foam article was demolded at 240 seconds (4 minutes) after the initial pour (detailed in next paragraph). Upon demold, the foam was placed through a mechanical crusher or tested for Force-to-Crush (FTC) measurements or allow to cool down to determine dimensional stability (detailed below).

Foam made with each catalyst set were mechanically crushed 1 minute after demold using a Black Brothers Roller crusher set to a gap of 2.54 cm. Crushing was conducted three times on each part, rotating the foam 90 degrees after each pass through the rollers. All parts produced for physical testing were allowed to condition for at least seven days in a constant temperature and humidity room (23±2° C., 50±2% relative humidity).

FTC measurements were conducted 45 seconds after demold. The pad was removed from the mold, weighed and placed in the FTC (force to crush) apparatus (model number ISCO HGI Pressure Pump). The force detection device is equipped with a 2.2 kg capacity pressure transducer mounted between the 323 cm$^2$ circular plate cross head and the drive shaft. The actual force is shown on a digital display. This device is operated in accordance with ASTM D-3574, Indentation Force Deflection Test and provides a numerical value of freshly demolded foam's initial hardness or softness. The pad was compressed to 50 percent of its original thickness at a cross-head velocity of 275 mm per minute with the force necessary to achieve the highest compression cycle recorded in Newton's. Ten compression cycles were completed. A cycle takes approximately 30 seconds to complete.

Example 1

Synthesis of N, N-Bis-(dimethylaminopropyl)-N-(3-aminopropyl)-amine

In the first step, a 1000 ml stainless steel reactor was charged with 424 g of bis(dimethylaminopropyl) amine and 23 g of water. The reactor was purged with nitrogen, heated up to 75° C. and 126 g of acrylonitrile was slowly fed in the reactor over a period of 1.5 hours. After all acrylonitrile was transferred into the reactor the temperature was maintained at 75° C. for an additional 4.0 hours. The reaction mixture was allowed to cool down to 25° C. and the product was removed from the reactor and analyzed by gas chromatography (GC) giving 96% yield of desired product 2-cyanoethyl-bis(dimethylaminopropyl)amine. In the second step, a 1000 ml stainless steel reactor was charged with 198 g of isopropanol and 6.9 g of standard Raney-Cobalt catalyst. The reactor was purged with nitrogen three times and the temperature was increased to 120° C. The reactor was pressurized with 800 psi of hydrogen and cyanoethyl-bis(dimethylaminopropyl)amine (344 g) was fed in the reactor at a rate of about 100 ml per hour for a period of about 4 hours. Once transfer of cyanoethyl-bis(dimethylaminopropyl)amine was completed the temperature was increased to 130° C. and hold for one hour. The product was analyzed by GC yielding 93 percent yield of desired product N, N-bis-(dimethylaminopropyl)-N-(3-aminopropyl)-amine (amine-1) with the remainder being unreacted precursor.

Example 2

Synthesis of N, N-Bis-(dimethylaminopropyl)-N-(3-aminopropyl)-urea

Amine-1 and urea (1:1 molar ratio) was charged into a 4-neck round bottom flask and the flask was then purged with nitrogen. A condenser on top of the flask was filled with ice water mix and a scrubber that consumed the ammonia by-product as it bubbled through a 30% acetic acid solution. Temperature of the reaction was increased to 120° C. with mechanical stirring. The reaction is then held at 120° C. for 90 min during which the solution changed from white opaque to yellow clear solution. All the volatiles are then removed under vacuum on rotovap before the final product is collected.

Example 3

Synthesis of Bis-[N, N-Bis-(dimethylaminopropyl)-N-(3-aminopropyl)]-urea

Amine-1 and urea (2:1 molar ratio) was charged into a 4-neck round bottom flask which was then purged with nitrogen. A condenser on top of the flask was filled with ice water mix and a scrubber that will consume the ammonia by-product is filled with 30% acetic acid solution. The mixture was mechanically stirred and the temperature was increased to 120° C. The reaction was then held at 120° C. for 90 min during which the solution changed from white opaque to yellow clear solution. Then, the temperature of the reaction was increased to 155° C. The reaction was held at 155° C. for 90 min during which the reaction changed from light yellow clear solution to dark orange clear solution. All the volatiles were then removed under vacuum on rotovap before the final product is collected.

Example 4

Amine-1 (N, N-Bis-(dimethylaminopropyl)-N-(3-aminopropyl)-amine) was charged into a stainless steel reactor and the reactor was sealed and then purged with nitrogen. Propylene oxide (2:1 propylene oxide to amine molar ratio) was charged into an ISCO pump. The temperature of the reactor was increased to 140° C. and 2.1 equivalent of propylene oxide was charged into the reactor via the ISCO pump over 2.5 h, during which the pressure of the reactor was increased. After the feeding was completed, the reaction temperature was held at 140° C. until the drop of pressure stops (4 hours). The heating is then stopped and vent the reactor after cooling. All the volatiles were then removed under vacuum on rotovap before the final product was collected.

Example 5

Amine-1 (N, N-Bis-(dimethylaminopropyl)-N-(3-aminopropyl)-amine) was charged into a steel reactor equipped with a mechanical stirrer and the reactor was sealed and then purged with nitrogen. Propylene oxide was charged into an ISCO pump. The temperature of the reactor was increased to 140° C. and 1.1 equivalent of propylene oxide was charged into the reactor via the ISCO pump over 80 min, during which the pressure of the reactor increased. After the feeding was completed, the reaction temperature was held at 140° C. until the drop of pressure stopped (1.5 h). The heating was then stopped and the reactor was vented after cooling. All the volatiles were then removed under vacuum on rotovap before the final product is collected.

Example 6

Foam Rate of Rise Kinetics and Use Level Comparison for Catalysts Made in Examples 2 to 5

Foaming performance can be evaluated by comparing the foam height versus time for standards and new amine catalyst. Foam height profile can be measured by automated rate of rise equipment, utilizing free-rise cup foam samples with a FOMAT sonar rate-of-rise device (hereafter referred to as a "ROR"). The FOMAT device comprises a sonar sensor that measures and records the height in millimeters (mm) of the rising foam sample versus time in seconds (s), directly after mixing all components of the formulation. The FOMAT standard software generates both height versus time plots and velocity versus time plots. These plots are useful for comparing the relative reactivity of different catalyst formulations. Flexible foam can be prepared by combining a total weight of about 300 g of the ingredients in Table 2 other than the isocyanate in a 32-oz (951 ml) paper cup. This premix formulation is then mixed for about 10 seconds at about 6,000 rpm using an overhead stirrer fitted with a 2-inch (5.1 cm) diameter stirring paddle. Sufficient toluene diisocyanate is then added to achieve the desired Isocyanate Index of about 100, and the formulation is mixed well for about another 6 seconds at about 6,000 rpm using the same stirrer. The cup is then placed under the FOMAT sensor. The start time for ROR measurement is automated for the FOMAT and begins directly after the end of the final mixing. Once the cup is placed under the ROR, the chemical mixture begins to polymerize. Since the walls of the cup restrict the expansion in all but the vertical direction, this expansion manifests itself in this experiment as an increase in height with passing time.

TABLE 2

| Premix Components | |
| --- | --- |
| Component | PPHP |
| SPECFLEX ® NC 630[1] Polyol | 50 |
| SPECFLEX ® NC 700[2] Polyol | 50 |
| Water | 3.0 |
| DABCO ® DC6070[3] | 0.60 |
| Low emissions silicon surfactant | |
| Catalyst[4] | Varied |
| Diethanolamine (crosslinker) | 0.70 |
| Toluene diisocyanate | To provide NCO index = 100 |

[1]High functionality capped polyether polyol of high molecular weight, functionality, and primary hydroxyl content with a base polyol molecular weight of about 5500, available from Dow Chemical Company, Midland, MI.

[2]Grafted polyether polyol containing copolymerized styrene and acrylonitrile, base polyol molecular weight about 4800, available from Dow Chemical Company, Midland, MI.

[3]Silicone surfactant is available from Air Products and Chemicals, Inc.

[4]The amine catalyst is available from Air Products and Chemicals, Inc.

This increase in height can also be displayed as a rate of changing height (velocity) versus time. Useful comparisons can be made on the rate of the foaming reaction by recording the time required after mixing for the foam to reach a standard height (TOC=Top of the Cup), the maximum foam rise velocity, the time after mixing that was required to achieve the maximum velocity as well as the string gel time (SGT) which is the time at which the polymerizing mass is able to form polymer strings when touched with a wooden tongue suppressor.

TABLE 3

| Foam Top of the Cup and String Gel Time in Seconds | | | | |
| --- | --- | --- | --- | --- |
| Run # | Gel Catalyst | pphp | TOC (sec) | SGT (sec) |
| 1 | DABCO ® NE1070[1] | 0.70 | 40 | 63 |
| 2 | Example 2 Amine | 0.35 | 38 | 62 |
| 3 | Example 3 Amine | 0.35 | 36 | 63 |
| 4 | Example 4 Amine | 0.30 | 36 | 61 |
| 5 | Example 5 Amine | 0.30 | 39 | 63 |

[1]DABCO ®NE1070 is a mixture of N,N-dimethylaminopropylurea and bis(N,N-dimethylaminopropyl)urea in polyethylene glycol with average MW = 200 (PEG-200) catalyst commercially available from Air Products and Chemicals, Inc. Rate of rise data performed in all cases with 0.17 pphp of blowing amine catalyst N,N,N-trimethyl-N-3-aminopropyl-bis(aminoethyl) ether

Example 7

Physical Properties of Polyurethane Foam Made with Catalysts of Examples 2 to 5

Foam pads were prepared by adding a tertiary amine catalyst to about 302 g of a premix (prepared as in Table 2) in a 32 oz (951 ml) paper cup. The formulation was mixed for about 10 seconds at about 6,000 RPM using an overhead stirrer fitted with a 2-inch (5.1 cm) diameter stirring paddle. The toluene diisocyanate was then added, and the formulation was mixed well for about another 6 seconds at about 6,000 RPM using the same stirrer, after which it was poured into a pre-heated mold at 70° C. and demolded after 4 minutes. The foam pads were removed from the mold, hand crushed, weighed and machine crushed at 75% pad thickness. Foam pads were stored under constant temperature and humidity condition for 48 hours before being cut and tested.

TABLE 4

Polyurethane TDI Flexible Molded Data

| Run# | Gel Catalyst | Gel Cat pphp | SG (sec) | Ext (sec) |
|---|---|---|---|---|
| 1 | NE1070[2] | 0.70 | 60 | 50 |
| 5 | Example 2 Amine | 0.35 | 64 | 49 |
|   | Example 3 Amine | 0.35 | 63 | 50 |
| 7 | Example 4 Amine | 0.30 | 47 | 59 |
| 8 | Example 5 Amine | 0.30 | 50 | 60 |

[1]Mold data performed in all cases with 0.17 pphp of blowing amine catalyst N,N,N'-trimethyl-N'-3-aminopropyl-bis(aminoethyl) ether.
Dabco ®NE1070[2] a mixture of mono and bis-dimethylaminopropyl urea dissolved in polyethylene glycol-200

TABLE 5

Physical Properties of TDI Polyurethane Flexible Molded Foam with 40 Kg/m³ Density and Index 100

| Test | Sample Conditions | Test Method | Units | NE1070 | Example 2 | Example 3 | Example 4 | Example 5 |
|---|---|---|---|---|---|---|---|---|
| Section Density | Ambient | ASTM D3574-A | lbs/ft3 | 2.37 | 2.73 | 2.77 | 2.41 | 2.44 |
| Section Density | Ambient | ASTM D3574-A | (kg/m3) | 37.93 | 43.72 | 44.37 | 38.62 | 39.10 |
| Air Flows | Ambient | ASTM D3574-G | SCFM | 3.55 | 3.29 | 3.14 | 3.29 | 3.33 |
| Air Flows | Ambient | ASTM D3574-G | UM | 100.54 | 93.10 | 88.78 | 93.03 | 94.24 |
| ILD 25% | Ambient | ASTM D357481 | lbsf | 50.76 | 46.10 | 44.43 | 52.99 | 49.93 |
| ILD 25% | Ambient | ASTM D3574-B1 | N | 225.80 | 205.07 | 197.64 | 235.71 | 222.10 |
| ILD 65% | Ambient | ASTM D357481 | lbsf | 118.64 | 125.91 | 125.13 | 115.70 | 120.25 |
| ILD 65% | Ambient | ASTM D357481 | N | 527.74 | 560.07 | 556.60 | 514.68 | 534.92 |
| ILD 25% Return | Ambient | ASTM D357481 | lbsf | 42.17 | 38.15 | 37.01 | 43.44 | 41.43 |
| ILD 25% Return | Ambient | ASTM D357481 | N | 187.60 | 169.72 | 164.62 | 193.25 | 184.30 |
| Support Factor | Ambient | ASTM D357481 | ratio | 2.34 | 2.73 | 2.82 | 2.18 | 2.41 |
| Resilience | Ambient | ASTM D3574-H | % | 57 | 54 | 52 | 57 | 53 |
| ALLS (70% Preflex) | Volkswagen[2] | ISO-3386-1 | % | −54.88 | −61.16 | −58.53 | −56.85 | −56.52 |
| Tensile Strength | Ambient | DIN 53571 | psi | 19.73 | 20.66 | 23.64 | 21.91 | 20.20 |
| Tensile Strength | Ambient | DIN 53571 | kPa | 136.03 | 144.32 | 165.11 | 151.11 | 139.28 |
| Tensile Elongation | Ambient | DIN 53571 | % | 92.48 | 89.13 | 97.83 | 99.08 | 79.17 |
| HA Tensile Strength | Volkswagen | DIN 53571 | psi | 4.52 | 7.07 | 6.29 | 6.70 | 5.22 |
| HA Tensile Strength | Volkswagen | DIN 53571 | kPa | 31.15 | 48.73 | 43.40 | 46.21 | 35.96 |
| HA Elongation | Volkswagen | DIN 53571 |  | 41.37 | 62.72 | 60.12 | 57.66 | 52.55 |
| Tear Strength | Ambient | ASTM D3574-F | lbs | 1.88 | 1.71 | 1.69 | 1.56 | 1.64 |
| Tear Strength | Ambient | ASTM D3574-F | N/m | 328.39 | 299.71 | 296.10 | 273.93 | 287.21 |
| 50% Comp. Sets | 70° C. dry oven | ASTM D3574-D | % | 8.51 | 9.00 | 8.79 | 8.38 | 8.68 |
| 50% HA Comp. Sets | Volkswagen | ASTM D3574-D | % | 22.77 | 27.82 | 20.00 | 17.60 | 1739 |

Mold data performed in all cases with 0.17 pphp of blowing amine catalyst N,N,N'-trimethyl-N'-3-aminopropyl-bis(aminoethyl) ether[2] Volkswagen ageing procedure: Place samples to be tested in a dry oven at 90° C. for 24 hours for drying. Once dried. age samples for 200 hours 90° C. and 100% relative humidity. Samples are then dried after.

Table 5 shows the ambient and humid aged physical properties of flexible molded polyurethane pads made with the standard composed of reactive gelling amine catalysts Dabco® NE1070 catalyst as well as new non-emissive catalysts of examples 2 to 5. Table 5 shows that the ambient physical properties were very similar providing foam pads with excellent physical properties. Table 5 also shows the physical properties after humid ageing using a procedure. The evaluation showed new gelling catalysts from examples 2 to 5 performed similarly to a standard reactive catalyst DABCO® NE1070, Foams made using the inventive catalyst has a Tensile Strength (kPa)≥70; Elongation (%)≥70; 50% CS (%)≤18; and a 50% HACS (%)≤18.

Example 8

Ageing of PU Foam Made with Amine-3 and Amine-4 When in Contact with a Polycarbonate Surface Foam samples were made with amine catalysts of Examples 3 and 4 as well as emissive standard Dabco®33LV and Dabco® NE1070 catalyst and placed into contact with polycarbonate surfaces and aged under 100% percent humidity at 90° C. for 6 days to determine if the polycarbonate surface (Makrolon® GP Clear 099 4 mm with no anti-UV agent) is adversely affected. The foam samples were made using the following general formulations:

TABLE 6

Foam Samples For Polycarbonate Test

| | Foam Sample | | | | | | | |
|---|---|---|---|---|---|---|---|---|
| | 1 | 2 | 3 | 4 | 5 | 6 | 7 | 8 |
| Lupranol ®2095 | 85 | 85 | 85 | 85 | 85 | 85 | 85 | 85 |
| Lupranol ®4003/1 | 15 | 15 | 15 | 15 | 15 | 15 | 15 | 15 |
| DEOA | 1.2 | 1.2 | 1.2 | 1.2 | 1.2 | 1.2 | 1.2 | 1.2 |
| Water | 3.0 | 3.0 | 3.0 | 3.0 | 3.0 | 3.0 | 3.0 | 3.0 |
| Dabco ®DC6070 | 1.0 | 1.0 | 1.0 | 1.0 | 1.0 | 1.0 | 1.0 | 1.0 |
| Blow Catalyst | 0.2 | 0.2 | 0.2 | 0.2 | 0.2 | 0.2 | 0.2 | 0.2 |
| Dabco ®33LV | 0.55 | | | | 0.55 | | | |
| Dabco ®NE1070 | | 1.0 | | | | 1.00 | | |
| Amine-3 | | | 0.65 | | | | 0.65 | |
| Amine-4 | | | | 0.75 | | | | 0.75 |
| Lupranat ®T80 | Index 65 | | | | Index 90 | | | |

Lupranol ®2095 is a trifunctional high reactive polyether polyol having primary OH groups commercially available from BASF.
Luprano ®4003/1 is a polyether polyol which has been grafted with a styrene-acrylonitrile polymer (SAN) with 45% solid content and having mainly primary OH groups supplied commercially by BASF.
Dabco ®DC6070 is a standard silicone surfactant used in cold cure flexible molded TDI polyurethane foam supplied commercially by Air Products.
Blow Catalyst is N,N,N'-trimethyl-N'-3-aminopropyl-bis(aminoethyl) ether.
Dabco ®33LV is a 33% solution of triethylenediamine (TEDA) in dipropylene glycol.
Dabco ®NE1070 is a mixture of dimethylaminopropylurea and bis(dimethylaminopropyl)urea in polyethylene glycol MW = 200.
Lupranat ®T80 is toluenediisocyanate mixture containing 80% 2,4-isomer and 20% 2,6-isomer supplied commercially by BASF.

TABLE 7

Mass Change in Polycarbonate Test Specimen When Humid Aged in Contact with Flexible Molded Polyurethane Foam Made with Various Catalysts

| TDI Foam | Mass Change | | | |
|---|---|---|---|---|
| Index | Index 90 | | Index 65 | |
| Polycarbonate Weight Loss | Δ [mg] | [%] | Δ [mg] | [%] |
| Blank PC Plate | 19.19 | 0.35 | 19.19 | 0.35 |
| Dabco ®NE1070 | −195.71 | −3.56 | −363.79 | −6.66 |

TABLE 7-continued

Mass Change in Polycarbonate Test Specimen When Humid Aged in Contact with Flexible Molded Polyurethane Foam Made with Various Catalysts

| TDI Foam | Mass Change | | | |
|---|---|---|---|---|
| Index | Index 90 | | Index 65 | |
| Polycarbonate Weight Loss | Δ [mg] | [%] | Δ [mg] | [%] |
| Dabco ®33LV | 18.61 | 0.35 | 18.65 | 0.34 |
| Amine-4 | 17.44 | 0.33 | 16.88 | 0.31 |
| Amine-3 | 9.89 | 0.18 | 13.87 | 0.26 |

Referring now to FIG. 1, FIG. 1 illustrates a foam at index 90 shows that extensive foam damage and staining was observed for standard catalyst Dabco® NE1070 while new amine-3 and amine-4 shows very minor or no impact of foam coloring and integrity. Foam exposed to Dabco®33LV catalyst also showed no damage and coloring probably due to migration out of the foam specimen during the process and therefore no impact on polycarbonate. Referring now to FIG. 2, FIG. 2, extensive polycarbonate damage can be seen when using Dabco® NE1070 catalyst as gelling catalysts while minimal impact is seen for inventive amine-3 and amine-4. In particular, amine-4 showed almost no damage.

These observations were confirmed by measuring the changes in weight of the polycarbonate specimen shown in Table-7 where polycarbonate specimens exposed to foam made with Dabco® NE1070 catalyst showed the largest decrease in weight while amine-3 and amine-4 showed minimal change. As shown in Table 7, these changes are more pronounced at lower index (Index 65) (e.g., without wishing to be bound by any theory or explaination, it is believed due to poor amine immobilization), and where the polycarbonate specimen showed the largest weight loss when using Dabco@NE1070 catalyst. Nevertheless, amine-3 and amine-4 showed negligible mass change consistent with minimal or no damage to the polycarbonate specimen. In particular, amine-4 showed the smallest change. In all cases, emissive catalyst Dabco®33LV showed small weight change (e.g., without wishing to be bound by any theory or explanation, it is believed due to migration out of the foam specimen and not being in contact with the polycarbonate specimen). Referring now to FIG. 5, FIG. 5 shows the experimental set up for the foam/polycarbonate ageing procedure.

Example 9

Physical Properties of Polyurethane Foam Made

Foam samples were made with amine catalysts of examples 3 and 4 to determine the physical properties at various indexes and densities. The foam testing was done using the following general formulation:

TABLE 8

Foam Samples For Physical Property Evaluation

| | Foam Sample | | | | | | | |
|---|---|---|---|---|---|---|---|---|
| | 5 | 6 | 7 | 8 | 9 | 10 | 11 | 12 |
| Lupranol ®2095 | 85 | 85 | 85 | 85 | 85 | 85 | 85 | 85 |
| Lupranol ®4003/1 | 15 | 15 | 15 | 15 | 15 | 15 | 15 | 15 |
| DEOA | 1.2 | 1.2 | 1.2 | 1.2 | 1.2 | 1.2 | 1.2 | 1.2 |
| Water | 3.0 | 3.0 | 3.0 | 3.0 | 3.0 | 3.0 | 3.0 | 3.0 |
| Dabco ®DC6070 | 1.0 | 1.0 | 1.0 | 1.0 | 1.0 | 1.0 | 1.0 | 1.0 |
| Blow Catalyst | 0.2 | 0.2 | 0.2 | 0.2 | 0.2 | 0.2 | 0.2 | 0.2 |
| Dabco ®33LV | 0.55 | | | | 0.55 | | | |
| Dabco ®NE1070 | | 1.00 | | | | 1.0 | | |
| Amine-3 | | | 0.65 | | | | 0.65 | |
| Amine-4 | | | | 0.75 | | | | 0.75 |
| Lupranat ®T80 | Index 90 | | | | Index 105 | | | |

Lupranol ®2095 is a trifunctional high reactive polyether polyol having primary OH groups commercially available from BASF.
Luprano ®4003/1 is a polyether polyol which has been grafted with a styrene-acrylonitrile polymer (SAN) with 45% solid content and having mainly primary OH groups supplied commercially by BASF.
Dabco ®DC6070 is a standard silicone surfactant used in cold cure flexible molded TDI polyurethane foam supplied commercially by Air Products.
Blow Catalyst is N,N,N'-trimethyl-N'-3-aminopropyl-bis(aminoethyl) ether.
Dabco ®33LV is a 33% solution of triethylenediamine (TEDA) in dipropylene glycol.
Dabco ®NE1070 is a mixture of dimethylaminopropylurea and bis(dimethylaminopropyl)urea in polyethylene glycol MW = 200.
Lupranat ®T80 is toluenediisocyanate mixture containing 80% 2,4-isomer and 20% 2,6-isomer supplied commercially by BASF.

TABLE 9

Physical Properties for Flexible Molded Polyurethane Foam at Index 90 and 40 Kg/m$^3$ Density

| Catalyst | | | | Dabco NE1070 | | Dabco 33LV | | Amine-4 | | Amine-3 | |
|---|---|---|---|---|---|---|---|---|---|---|---|
| Property | Units | Conditions | Method | | SD | | SD | | SD | | SD |
| Tensile Strength | [kPa] | Ambient | DIN 53571 | 95.6 | 4.1 | 107.4 | 6.7 | 87.4 | 0.8 | 100.8 | 3.7 |
| Tensile Elongation | [%] | Ambient | DIN 53571 | 143.7 | 8.2 | 146.0 | 6.40 | 143.3 | 4.9 | 176.74 | 9.1 |
| HA Tensile Strength | [kPa] | Volkswagen | DIN 53571 | 3.5 | 0.6 | 1.6 | 0.5 | 3.8 | 0.8 | n.a. | n.a. |
| HA Tensile Elongation | [%] | Volkswagen | DIN 53571 | 21.78 | 2.9 | 20.0 | 4.63 | 44.80 | 7.0 | n.a. | n.a. |
| 50% HA Compression Set | [%] | Volkswagen | ASTM D3574-D | 39.54 | 2 | 15.1 | 0.76 | 33.62 | 1.5 | 32.07 | 2.3 |
| CLD | [kPa] | Ambient | ASTM D3574-C | 1.52 | 0.03 | 2.1 | 0.10 | 1.32 | 0.05 | 1.54 | 0.12 |
| HA CLD | [kPa] | Volkswagen | ASTM D3574-C | 0.34 | 0.02 | 1.67 | 0.10 | 0.33 | 0.04 | 0.56 | 0.08 |
| HALLS | [%] | Volkswagen | ISO 3386-1 | −78.0 | 1.1 | −22.5 | 1.3 | −74.8 | 2.4 | −63.5 | 2.77 |
| Foam Tear | [N/mm] | Ambient | ASTM D3574-F | 0.45 | 0.03 | 0.38 | 0.01 | 0.41 | 0.01 | 0.38 | 0.01 |

TABLE 10

Physical Properties for Flexible Molded Polyurethane Foam at
Index 105 and 45 Kg/m3 Density

| Catalyst | | | | Dabco NE1070 | | Dabco 33LV | | Amine-4 | | Amine-3 | |
|---|---|---|---|---|---|---|---|---|---|---|---|
| Property | Units | Conditions | Method | | SD | | SD | | SD | | SD |
| Tensile Strength | [kPa] | Ambient | DIN 53571 | 119.0 | 6.7 | 111.5 | 7.10 | 122.10 | 5.86 | 118.87 | 4.38 |
| Tensile Elongation | [%] | Ambient | DIN 53571 | 111.7 | 5.35 | 131.41 | 4.88 | 102.21 | 5.78 | 130.68 | 8.44 |
| HA Tensile Strength | [kPa] | Volkswagen | DIN 53571 | 1.50 | 0.09 | 1.89 | 0.63 | 1.34 | 0.35 | n.a. | n.a. |
| HA Tensile Elongation | [%] | Volkswagen | DIN 53571 | 10.3 | 0.62 | 16.87 | 4.69 | 11.08 | 2.44 | n.a. | n.a. |
| 50% HA Compression Set | [%] | Volkswagen | ASTM D3574-D | 37.9 | 0.96 | 19.5 | 0.75 | 41.28 | 2.07 | 46.75 | 0.96 |
| CLD | [kPa] | Ambient | ASTM D3574-C | 2.76 | 0.04 | 2.85 | 0.05 | 2.74 | 0.13 | 2.68 | 0.04 |
| HA CLD | [kPa] | Volkswagen | ASTM D3574-C | 0.16 | 0.05 | 1.96 | 0.02 | 0.55 | 0.05 | 0.62 | 0.14 |
| HALLS | [%] | Volkswagen | ISO 3386-1 | −94.21 | 1.62 | −31.09 | 1.40 | −79.94 | 1.62 | −76.90 | 4.87 |
| Foam Tear | [N/mm] | Ambient | ASTM D3574-F | 0.45 | 0.03 | 0.39 | 0.04 | 0.43 | 0.04 | 0.29 | 0.01 |

[1]foam deteriorated so no reliable measurement was possible.

Tables 9 and 10 show a summary of physical properties for amine-3 and amine-4 as well as standards emissive (DABCO@33LV) and non-emissive (DABCO@NE1070) catalysts. In particular, amine-4 performs very well under humid aged conditions showing excellent physical properties. This is exemplified in tables 9 and 10 where excellent humid aged tensile, elongations and compression sets are observed for amine-4.

Example 10

Emissions Measurement on Flexible Molded Polyurethane Foam Made

Foam pads were prepared as described in Example 8 and 9 using isocyanate indexes of 90 and 65. Emission from foam was measured using thermodesorption analysis and the substances emitted at 90° C. (VOC) and 120° C. (FOG) were quantified according to VDA 278 method. For this purpose a sample of the test material was heated in a current of inert gas and the substances released were frozen out in the refrigerated injector of the gas chromatograph. The mixture was then passed through the gas chromatographic column and the total emissions quantified. The VOC and FOG were measured with each sample according to the table shown below. Quantification of the gaseous emissions (VOC) was made against an external toluene standard while the condensable emissions (FOG) were quantified against hexadecane (n-$C_{16}$-alkane). The concentrations are reported in ppm below as total emissions in toluene and hexadecane equivalents.

TABLE 11

Emissions from TDI Based Flexible Molded Polyurethane Foam at Index 90 and Index 65

| | Index | | | | | | | |
|---|---|---|---|---|---|---|---|---|
| | Index 90 | | | | Index 65 | | | |
| Catalysts | VOC | Amine | FOG | Amine | VOC | Amine | FOG | Amine |
| Dabco ®33 LV | 483 | 74 | 249 | ND | 648 | 54 | 396 | ND |
| Dabco ®NE1070 | 316 | ND | 584 | 208 | 1064 | ND | 1354 | 730 |
| Amine-4 | 461 | ND | 282 | ND | 730 | ND | 652 | ND |
| Amine-3 | 455 | ND | 345 | ND | 890 | ND | 600 | ND |

Tables 11 shows emission results according to the new VDA278 method described above at low isocyanate indexes of 90 and 65. Thus, no amine emissions were detected with foam samples made with either amine-3 or amine-4.

Example 11

Dimensional Stability of Flexible Molded Polyurethane Foam Made with Amine-4 and Comparison with Standards Foam pads were prepared as described in Example 7 using the formulation shown in Table 12:

TABLE 12

Formulation for Polyurethane Flexible Molded Foam Dimensional Stability Test

| COMPONENT | PPHP |
|---|---|
| Specflex ®NC 630 | 55 |
| Specflex ®NC701 | 45 |
| Dabco ®DC6070 | 0.60 |
| Voranol ®CP-1421 | 0.60 |
| Water | 3.0 |
| DEOA | 0.70 |
| Dabco ®NE1070 | 0.70 |

TABLE 12-continued

Formulation for Polyurethane Flexible Molded Foam Dimensional Stability Test

| COMPONENT | PPHP |
|---|---|
| Blow Catalyst | 0.17 |
| Desmodur ®T80 | 100 |
| TDI Index | |

Specflex ®NC 630 is a high reactive polyether polyol having mainly primary OH groups commercially available from Dow.
Specflex ®NC701 is a polyether polyol which has been grafted with a styrene-acrylonitrile polymer (SAN) and having mainly primary OH groups supplied commercially by Dow.
Dabco ®DC6070 is a standard silicone surfactant used in cold cure flexible molded TDI polyurethane foam supplied commercially by Air Products.
Voranol ®CP-1421 is a cell opening polyol supplied commercially by Dow.
DEOA is diethanolamine crosslinker.
Blow Catalyst is N,N,N'-trimethyl-N'-3-aminopropyl-bis(aminoethyl) ether.
Dabco ®NE1070 is a mixture of dimethylaminopropylurea and bis(dimethylaminopropyl) urea in polyethylene glycol MW = 200.
Desmodur ®T80 is toluenediisocyanate mixture containing 80% 2,4-isomer and 20% 2,6-isomer supplied commercially by Covestro.

Hand mixed flexible molded foam were made using the components shown in formulation of Table 12. The mold was a typical physical property tool designed with internal dimensions of 40.6 cm×40.6 cm×10.2 cm. The mold has five vents, each approximately 1.5 mm in diameter, centered in each corner 10.0 cm from each edge and the geometric center of the lid. The mold was sprayed with a solvent-based release agent, prior to every pour and allowed to dry for one minute before pouring.

Foam pads were prepared by adding a tertiary amine catalyst to about 302 g of a premix (prepared by mixing all polyols, DEOA, DABCO® DC6070 and water) in a 32 oz (951 ml) paper cup according to formulation in Table 12. The formulation was mixed for about 10 seconds at about 6,000 RPM using an overhead stirrer fitted with a 2-inch (5.1 cm) diameter stirring paddle. Toluene diisocyanate was then added, and the formulation was mixed well for about another 6 seconds at about 6,000 RPM using the same stirrer, after which it was poured into a pre-heated mold at 70° C. and demolded after 4 minutes. The foam pads were removed from the mold, weighed and stored under constant temperature and humidity condition for 48 hours before being evaluated. The foam pads in this case were not crushed because the purpose of this experiment was to show the degree of dimensional stability (shrinkage) for each case. An amine catalyst able to provide foam with no shrinkage (dimensionally stable) is a highly desired feature to minimize foam scrap during manufacture.

TABLE 13

Dimensional Stability of Flexible Molded Polyurethane Foam

| Foam | Gelling Catalyst | Gelling Catalyst pphp | Blowing Catalyst[1] pphp | Ext Time (sec) | SGT (sec) | Observations |
|---|---|---|---|---|---|---|
| 1 | Dabco ®NE1070 | 0.70 | 0.17 | 43 | 62 | No Shrinkage |
| 2 | Dimethylaminopropyl-bis(2-hydroxypropyl)amine | 0.70 | 0.17 | 43 | 57 | Excessive Shrinkage |
| 3 | Amine-4 | 0.35 | 0.17 | 47 | 59 | No Shrinkage |
| 4 | Amine-3 | 0.30 | 0.17 | 42 | 59 | No Shrinkage |

[1]In all cases the blowing amine catalyst was N,N,N-trimethyl-N-3-aminopropyl-bis(aminoethyl) ether.
[2]EXT (sec) is the time in seconds for the foaming mass to extrude through one of the mold vents.
[3]SGT(sec) is the string gel time which is the time in seconds for the extruding foaming mass to form strings when touched with a wooden tongue suppressor Table 13 and FIG. 6 shows further additional advantages of amine-3 and amine-4 in providing foam pads with excellent dimensional stability showing no shrinkage in Foam-3 and Foam-4 when the part is removed from the mold.

While the invention has been described with reference to certain aspects or embodiments, it will be understood by those skilled in the art that various changes may be made and equivalents may be substituted for elements thereof without departing from the scope of the invention. In addition many modifications may be made to adapt the teachings of the invention without departing from the essential scope thereof. Therefore it is intended that the invention not be limited to the particular embodiment disclosed as the best mode contemplated for carrying out this invention but that the invention will include all embodiments falling within the scope of the appended claims.

The following is claimed:

1. A method for making an open cell flexible polyurethane foam comprising contacting a polyol component comprising at least one polyol and at least one copolymer polyol, and at least one isocyanate in the presence of at least one gelling catalyst and at least one blowing catalyst, and at least one component selected from the group consisting of at least one cell stabilizer, at least one blowing agent, at least one crosslinking agent, at least one chain extender, at least one pigment, at least one filler, at least one flame retardant, at least one transition metal catalyst, at least one alkali carboxylate salt, at least one alkali earth carboxylate salt, or any combination thereof; wherein all gelling catalysts used in the method are selected from the group consisting of N,N-bis(3-dimethylaminopropyl)-N-[3-aminopropyl-N',N'-bis(2-hydroxypropyl)]amine, N,N-bis(3-dimethylaminopropyl)-N-[3-aminopropyl-N',N'-bis(2-hydroxyethyl)]amine, or a combination thereof; wherein all blowing catalysts used in the method are selected from the croup consisting of N,N,N'-trimethyl-N'-3-aminopropyl-bis(aminoethyl)ether, 2-[N-(dimethylaminoethoxyethyl)-N-methylamino]ethanol, or a combination thereof; wherein the at least one gelling catalyst is present in an amount between 0.1 parts by weight per hundred parts by weight of the polyol component to 5 parts by weight per hundred parts by weight of the polyol component; and wherein the at least one blowing catalyst is present in an amount between 0.01 parts by weight per hundred parts of the polyol component to 2 parts by weight per hundred parts by weight of the polyol component.

2. A method for making an open cell flexible polyurethane foam comprising (i) combining a polyol component comprising at least one polyol and at least one copolymer polyol, at least one gelling catalyst, at least one blowing catalyst and at least one component selected from the group consisting of at least one cell stabilizer, at least one blowing agent, at least one crosslinking agent, at least one chain extender, at least one pigment, at least one filler, at least one flame retardant, at least one transition metal catalyst, at least one alkali carboxylate salt, at least one alkali earth carboxylate salt, or any combination thereof, to form a mixture, and (ii) reacting the mixture with at least one isocyanate, wherein all gelling catalysts used in the method are selected from the group consisting of N,N-bis(3-dimethylaminopropyl)-N-[3-aminopropyl-N',N'-bis(2-hydroxypropyl]amine, N,N-bis(3-dimethylaminopropyl)-N-[3-aminopropyl-N',N'-bis(2-hydroxyethyl]amine, or a combination thereof; and wherein all blowing catalysts used in the method are selected from the group consisting of N,N,N'-trimethyl-N'-3-aminopropyl-bis(aminoethyl)ether, 2-[N-(dimethylaminoethoxyethyl)-N-methylamino]ethanol, or a combination thereof; wherein the at least one gelling catalyst is present in an amount between 0.1 parts by weight per hundred parts by weight of the polyol component to 5 parts by weight per hundred parts by weight of the polyol component; and wherein at least one blowing catalyst is present in an amount between 0.01 parts by weight per hundred parts of the polyol component to 2 parts by weight per hundred parts by weight of the polyol component.

3. A foam produced by the method of making an open cell flexible polyurethane foam in accordance with claim 1.

4. A foam produced by the method of making an open cell flexible polyurethane foam in accordance with claim 2.

5. The method of claim 1, wherein the at least one polyol comprises at least one polyether polyol.

6. The method of claim 1, wherein the at least one copolymer polyol comprises at least one graft polyol, at least one polyurea modified polyol, or a combination thereof.

7. The method of claim 2, wherein the at least one polyol comprises at least one polyether polyol.

8. The method of claim 2, wherein the at least one copolymer polyol comprises at least one graft polyol, at least one polyurea modified polyol, or a combination thereof.

9. A method for making an open cell flexible polyurethane foam comprising contacting at least one polyol and at least one isocyanate in the presence of at least one gelling catalyst, at least one blowing catalyst, and at least one component selected from the group consisting of at least one cell stabilizer, at least one blowing agent, at least one crosslinking agent, at least one chain extender, at least one pigment, at least one filler, at least one flame retardant, at least one transition metal catalyst, at least one alkali carboxylate salt, at least one alkali earth carboxylate salt, or any combination thereof; wherein all gelling catalysts used in the method are selected from the group consisting of N,N-bis(3-dimethylaminopropyl)-N-[3-aminopropyl-N',N'-bis(2-hydroxypropyl)]amine, N,N-bis(3-dimethylaminopropyl)-N-[3-aminopropyl-N',N'-bis(2-hydroxyethyl)]amine, or a combination thereof; wherein all blowing catalysts used in the method are selected from the group consisting of N,N,N'-trimethyl-N'-3-aminopropyl-bis(aminoethyl)ether, 2-[N-(dimethylaminoethoxyethyl)-N-methylamino]ethanol, or a combination thereof; wherein the at least one gelling catalyst present in an amount between 0.1 parts by weight per hundred parts by weight of the at least one polyol to 5 parts by weight per hundred parts by weight of the at least one polyol; and wherein at least one blowing catalyst is present in an amount between 0.01 parts by weight per hundred parts of the at least one polyol to 2 parts by weight per hundred parts by weight of the at least one polyol.

10. The method of claim 9, wherein the at least one polyol comprises at least one polyether polyol.

\* \* \* \* \*